(12) United States Patent
Bandyopadhyay et al.

(10) Patent No.: US 8,545,559 B2
(45) Date of Patent: Oct. 1, 2013

(54) MODIFIED METAL MATERIALS, SURFACE MODIFICATIONS TO IMPROVE CELL INTERACTIONS AND ANTIMICROBIAL PROPERTIES, AND METHODS FOR MODIFYING METAL SURFACE PROPERTIES

(75) Inventors: Amit Bandyopadhyay, Pullman, WA (US); Susmita Bose, Pullman, WA (US)

(73) Assignee: Washington State University, Pullman, WA (US)

( * ) Notice: Subject to any disclaimer, the term of this patent is extended or adjusted under 35 U.S.C. 154(b) by 195 days.

(21) Appl. No.: 12/246,455

(22) Filed: Oct. 6, 2008

(65) Prior Publication Data
US 2009/0093881 A1    Apr. 9, 2009

Related U.S. Application Data

(60) Provisional application No. 60/978,064, filed on Oct. 5, 2007.

(51) Int. Cl.
*A61F 2/28*    (2006.01)

(52) U.S. Cl.
USPC ................... 623/16.11; 623/23.55

(58) Field of Classification Search
CPC ............................................. A61F 2/28
USPC ................... 623/16.11; 427/2.24
See application file for complete search history.

(56) References Cited

U.S. PATENT DOCUMENTS

| | | | | |
|---|---|---|---|---|
| 6,582,715 | B1 * | 6/2003 | Barry et al. | 424/422 |
| 6,881,227 | B2 * | 4/2005 | Jordanova-Spassova | 623/16.11 |
| 2006/0229715 | A1 * | 10/2006 | Istephanous et al. | 623/1.46 |
| 2007/0191962 | A1 * | 8/2007 | Jones et al. | 623/22.32 |
| 2007/0203584 | A1 | 8/2007 | Bandyopadhyay et al. | |
| 2009/0068272 | A1 | 3/2009 | Bandyopadhyay et al. | |
| 2009/0177282 | A1 * | 7/2009 | Bureau et al. | 623/16.11 |
| 2009/0220561 | A1 * | 9/2009 | Jin et al. | 424/423 |
| 2010/0303722 | A1 * | 12/2010 | Jin et al. | 424/9.1 |

FOREIGN PATENT DOCUMENTS

WO    WO-2007124511 A2    11/2007

OTHER PUBLICATIONS

Bao, Q. et al., Pulsed laser deposition and its current research status in preparing hydroxyapatite thin films, Applied Surface Science 252 (2005) 1538-1544.

(Continued)

*Primary Examiner* — Jason-Dennis Stewart
(74) *Attorney, Agent, or Firm* — Perkins Coie LLP

(57) ABSTRACT

The present disclosure is directed to modified metal materials for implantation and/or bone replacement, and to methods for modifying surface properties of metal substrates for enhancing cellular adhesion (tissue integration) and providing antimicrobial properties. Some embodiments comprise surface coatings for metal implants, such as titanium-based materials, using (1) electrochemical processing and/or oxidation methods, and/or (2) laser processing, in order to enhance bone cell-materials interactions and achieve improved antimicrobial properties. One embodiment comprises the modification of a metal surface by growth of in situ nanotubes via anodization, followed by electrodeposition of silver on the nanotubes. Other embodiments include the use of LENS™ processing to coat a metal surface with calcium-based bioceramic composition layers. These surface treatment methods can be applied as a post-processing operation to metallic implants such as hip, knee and spinal devices as well as screws, pins and plates.

13 Claims, 16 Drawing Sheets

(56) References Cited

OTHER PUBLICATIONS

Branemark, P-I et al., Osseointegrated implants in the Treatment of the Edentulous Jaw, Experience from a 10-year period, Almqvist & Wiksell International, Stockholm, Sweden, 1977, ISBN 91-22-00128-X.
Chao, M.J. et al., Preparation and characterization of in situ synthesized $B_4C$ particulate reinforced nickel composite coatings by laser cladding, Surface & Coatings Technology 201 (2006) 1102-1108.
Cheang, P. et al., Addressing processing problems associated with plasma spraying of hydroxyapatite coatings, Biomaterials 17 (1996) 537-544.
Cheng, G.J. et al., Bioceramic coating of hydroxyapatite on titanium substrate with Nd-YAG laser, Materials Science and Engineering C 25 (2005) 541-547.
Das, K. Anodized Titania: Processing and Characterization to Improve Cell-Materials Interactions for Load Bearing Implants, Ph.D. Dissertation, Washington State University, Materials Science Program, May 2007.
Das, K. et al., Surface modifications and cell-materials interactions with anodized Ti, Acta Biomaterialia (2007), doi:10.1016/j.actbio.2006.12.003.
Ducheyne, P., et al., Effect of calcium phosphate coating characteristics on early post-operative bone tissue ingrowth, Biomaterials 11 (1990) 531-540.
Dumbleton, J. et al., Hydroxyapatite-Coated Protheses in Total Hip and Knee Arthroplasty, J Bone Joint Surg Am 86 (2006) 2526-2540.
Feng, Q.L. et al., Antibacterial effects of Ag-HAp thin films on alumina substrates, Thin Solid Films 335 (1998) 214-219.
Geffen, A., Computational simulations of stress shielding and bone resorption around existing and computer-designed orthopaedic screws, Med Biol Eng Comput 40 (2002) 311-322.
Gong, D. et al., Titanium oxide nanotube arrays prepared by anodic oxidation, J Mater Res 16 (2001) 3331-3334.
Hamdi, M. et al., Coating of hydroxyapatite thin film by simultaneous vapor deposition, Thin Solid Films 377-378 (2000) 484-489.
Heine, R.W. et al., Principles of Metal Casting, Second Edition, McGraw-Hill Book Company, 1967.
Jalota, S. et al., Osteoblast proliferation on neat and apatite-like calcium phosphate-coated titanium foam scaffolds, Materials Science and Engineering C 27 (2007) 432-440.
Kawahara, K. et al., Antibacterial effect of silver-zeolite on oral bacteria under anaerobic conditions, Dental Materials 16 (2000) 452-455.
Kawashita, M. et al., Antibacterial silver-containing silica glass prepared by sol-gel method, Biomaterials 21 (2000) 393-398.
Khor, K.A. et al., Laser treatment of plasma sprayed HA coatings, Materials Science and Engineering A266 (1999) 1-7.
Klionsky, D.J. et al., Guidelines for the use and interpretation of assays for monitoring autophagy in higher eukaroyotes, Autophagy 4:2 (2008) 151-175.
Kokubo T. et al., Titania-based bioactive materials, Journal of the European Ceramic Society 27 (2007) 1553-1558.
Kunin, C.M., Detection, Prevention and Management of Urinary Tract Infections, Fourth Edition, Lea & Febiger, Philadelphia, 1987, 1-55.
Kurella, A. et al., A Multi-Textured Calcium Phosphate Coating for Hard Tissue via Laser Surface Engineering, JOM, Journal of the Minerals, Metals and Materials Society, 58 (2006) 64-66.
Li, T. et al., Hydroxyapatite coating by dipping method, and bone bonding strength, Journal of Materials Science: Materials in Medicine, 7 (1996) 355-357.
Lind, M. et al., Improved bone anchorage of hydroxyapatite coated implants compared with tricalcium-phosphate coated implants in trabecular bone in dogs, Biomaterials 20 (1999) 803-808.
Lusquinos, F. et al., Main characteristics of calcium phosphate coatings obtained by laser cladding, Applied Surface Science 247 (2005) 486-492.
Lusquinos, F. et al., Production of calcium phosphate coatings on Ti6AI4V obtained by Nd:yttrium-aluminum-garnet laser cladding, Journal of Applied Physics 90 (2001) 4231-4236.
Milev, A. et al., Morphological stability of hydroxyapatite precursor, Materials Letters 57 (2003) 1960-1965.
Ogose, A. et al., Histological Examination of β-Tricalcium Phosphate Graft in Human Femur, J Biomed Mater Res 63 (2002) 601-604.
Ohsawa K. et al., The expression of bone matrix protein mRNAs around β-TCP particles implanted into bone, J Biomed Mater Res 52 (2000)460-466.
Parkhutik, V.P. et al., Theoretical modelling of porous oxide growth on aluminum, J Phys D: Appl Phys 25 (1992) 1258-1263.
Petering H.G., Pharmacology and Toxicity of Heavy Metals: Silver, Pharmac Ther A 1 (1976) 127-130.
Rahn, R.O. et al., Ultraviolet irradiation of nucleic acids complexed with heavy atoms—II. Phosphorescence and photodimerization of DNA complexed with Ag, Photochemistry and Photobiology 18 (1973) 29-38.
Ritchie, J.A. et al., Antibacterial testing of metal ions using a chemically defined medium, Letters in Applied Microbiology 11 (1990) 152-154.
Rocca, M. et al., Osteointegration of hydroxyapatite-coated and uncoated titanium screws in long-term ovariectomized sheep, Biomaterials 23 (2002) 1017-1023.
Rokusek D. et al., Interaction of human osteoblasts with bioinert and bioactive ceramic substrates, J Biomed Mater Res 75A (2005) 588-594.
Roy, M. et al., Laser processing of bioactive tricalcium phosphate coating on titanium for load-bearing implants, Acta Biomaterialia 4 (2008) 324-333.
Stoch, A. et al., Electrophoretic coating of hydroxyapatite on titanium implants, Journal of Molecular Structure 596 (2001) 191-200.
Storrie, H. et al., Cellular response to zinc-containing organoapatite: An invitro study of proliferation, alkaline phosphatase activity and biomineralization, Biomaterials 26 (2005) 5492-5499.
Vallee, B.L. et al., Biochemical Effects of Mercury, Cadmium, and Lead, Annu Rev Biochem 41 (1972) 91-128.
Wang, D. et al., Microstructure of yttric calcium phosphate bioceramic coatings synthesized by laser cladding, Applied Surface Science 253 (2007) 4016-4020.
Wang, Y. et al., In situ fabrication of bioceramic composite coatings by laser cladding, Surface & Coatings Technology 200 (2005) 2080-2084.
Weng, J. et al., Intrinsic factors of apatite influencing its amorphization during plasma-spray coating, Biomaterials 16 (1995) 39-44.
Winn, S.R. et al., Establishing an Immortalized Human Osteoprecursor Cell Line: OPC1, Journal of Bone and Mineral Research 14 (1999) 1721-1733.
Xue, W. et al., In vivo evaluation of plasma sprayed hydroxyapatite coatings having different crystallinity, Biomaterials 25 (2004) 415-421.
Xue, W. et al., Preparation and cell-materials interactions of plasma sprayed strontium-containing hydroxyapatite coating, Surface & Coatings Technology 201 (2007) 4685-4693.
Yang, S. et al., Fabrication of nickel composite coatings reinforced with TiC particles by laser cladding, Surface & Coatings Technology 183 (2004) 254-260.
Yildirim O.S. et al., An investigation of the effects of hydroxyapatite coatings on the fixation strength of cortical screws, Medical Engineering & Physics 27 (2005) 221-228.
Zhang, W. et al., A Novel Bactericide with Silver Ion, Rare Metal Materials and Engineering 25 (1996) 49-51.

* cited by examiner

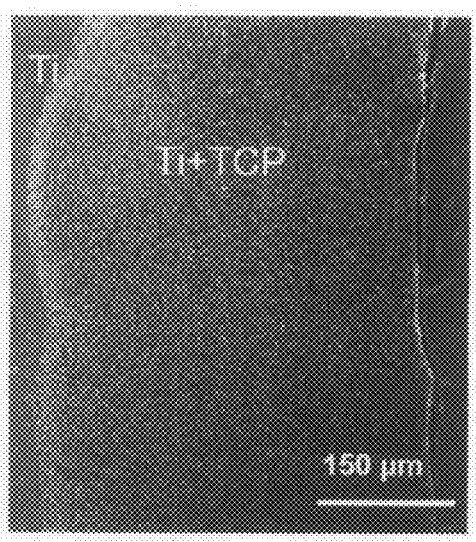 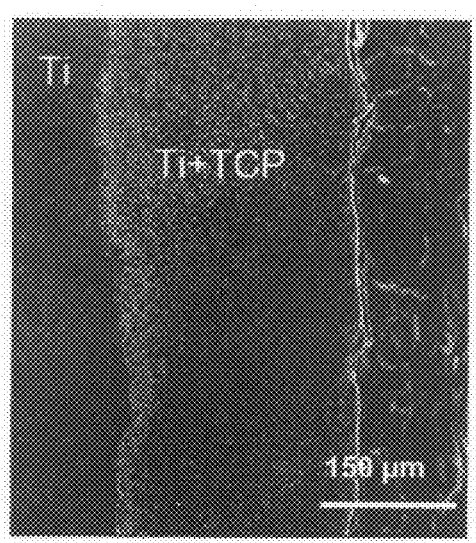
*FIG. 6A*  *FIG. 6B*

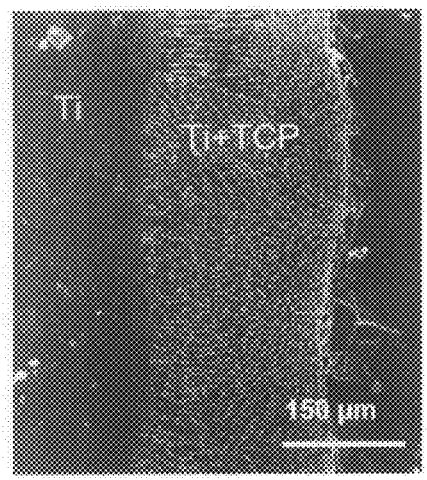 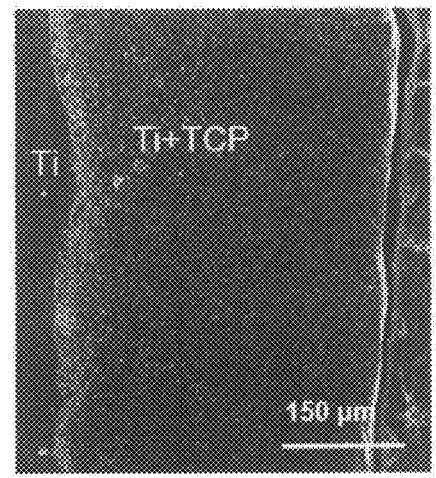
*FIG. 8A*            *FIG. 8B*

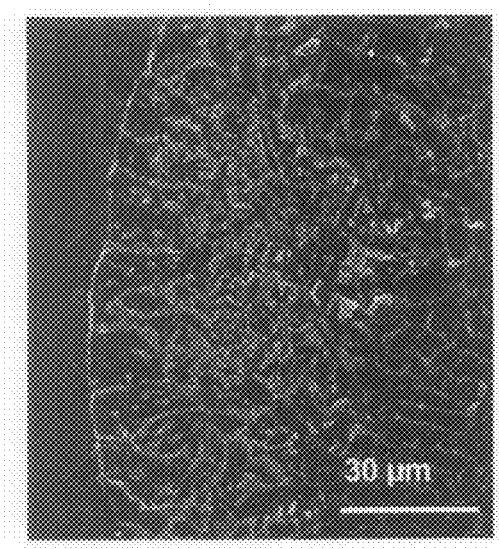 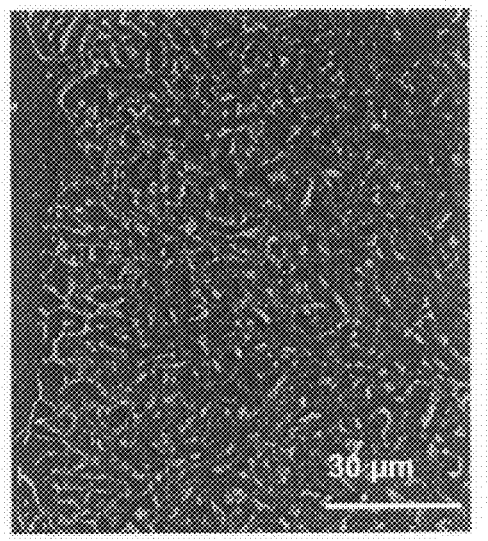
*FIG. 9A*  *FIG. 9B*

MODIFIED METAL MATERIALS, SURFACE MODIFICATIONS TO IMPROVE CELL INTERACTIONS AND ANTIMICROBIAL PROPERTIES, AND METHODS FOR MODIFYING METAL SURFACE PROPERTIES

CROSS-REFERENCE TO RELATED APPLICATIONS

The present application claims priority to U.S. Provisional Patent Application No. 60/978,064 filed Oct. 5, 2007, entitled "SURFACE MODIFICATIONS TO IMPROVE BONE CELL-MATERIALS INTERACTIONS AND ANTIMICROBIAL PROPERTIES," and incorporated herein in its entirety by reference. The present application incorporates the subject matter of (1) International Publication No. WO/2007/124511, entitled "RESORBABLE CERAMICS WITH CONTROLLED STRENGTH LOSS RATES," filed Apr. 25, 2007; (2) U.S. Publication No. 2007/0203584 A1, entitled "BONE REPLACEMENT MATERIALS," filed Feb. 14, 2007; and (3) U.S. patent application Ser. No. 12/211,005, entitled "MESOPOROUS CALCIUM SILICATE COMPOSITIONS AND METHODS FOR SYNTHESIS OF MESOPOROUS CALCIUM SILICATE FOR CONTROLLED RELEASE OF BIOACTIVE AGENTS," filed Sep. 15, 2008 in their entireties by reference.

STATEMENT REGARDING FEDERALLY SPONSORED RESEARCH

This work was partially funded by the Office of Naval Research (Grant No: N00014-01-05-0583) and the National Science Foundation (Grant No: CTS-0134476), and the United States government has, therefore, certain rights to the present invention.

TECHNICAL FIELD

The present disclosure is generally directed to modified metal materials for implantation and to methods for modifying surface properties of metal substrates for enhancing cellular adhesion and promoting growth of natural bone cells while preventing microbial activities.

BACKGROUND

Bone and joint replacement materials have been useful for treating a wide variety of musculoskeletal disorders. Replacement materials can, for example, be designed to restore both lost structure and function, particularly for load bearing applications. Bones in normal, healthy condition carry external joint and muscular loads by themselves. Following the insertion of orthopedic screws and/or implants, the natural bone in the treated region will share its load-carrying capacity with the implanted materials. Thus, the same load that had been originally born by the bone itself will now be carried by the 'composite' new structure. For load bearing screws and implants, clinically available devices are typically metallic.

The requirements for orthopedic metallic implants can be broadly categorized as (1) biocompatibility between the material and the surrounding environment with little or no adverse cytotoxicity and tissue reaction; and (2) the mechanical and physical properties necessary to achieve the desired biophysical function. Some desired properties are, for example, low modulus, high strength, good ductility, excellent corrosion resistance in the body fluid medium, high fatigue strength and good wear resistance. Titanium (Ti) and its alloys are widely used in orthopedic and dental implants because of favorable mechanical properties, corrosion resistance, and biocompatibility. However, Ti is a bioinert material having minimal interaction with the surrounding tissue. Accordingly, osseointegration with Ti implants, which requires a time-dependent kinetic modification of the surface of the implant, can take a long time.

Successful implantation challenges can also occur when the metallic implant material is significantly stiffer than the adjacent bone. Internal load bearing functionality naturally performed by the bone, can now be mainly supported by implanted screws or other structural implants. Such stress "shielding" of the natural bone can, in some instances, alter the normal stress stimuli for bone growth, and the reduction of bone stresses relative to the natural situation causes bone to adapt itself by reducing its mass in a process of resorption around the implant. This resorption/bone loss effect can cause micromotion of the screws/implants in response to external loads and could further damage the interfacing bone layer and anchorage performances subsequent to possible loosening of the screw/implant [1].

Infection is also a possible side effect often associated with implants and bone replacement surgeries. Infections, in some cases, may require removal of a surgically administered prosthesis or cause a significant delay in post-surgical healing. This is often due to the accumulation of microbial plaque or biofilm development on implants, screws or plates, which can contribute to recurrent infections as well as cause bone loss or prevent the necessary bone deposition for anchoring the surgical implant.

BRIEF DESCRIPTION OF THE DRAWINGS

In order that advantages of the disclosure will be readily understood, a description of aspects of the disclosure will be rendered by reference to specific embodiments and the appended drawings. Understanding that these drawings depict only typical embodiments of the disclosure and are not therefore to be considered to be limiting of its scope, the disclosure will be described and explained with additional specificity and detail through the use of the accompanying drawings.

FIGS. 6A-B are SEM micrographs of TCP coating layers on Ti substrates fabricated using LENS™ at a scan speed of 15 mm/sec. with a powder feed rate of 13 g/min. and at (A) 500W laser power, and (B) 400W laser power in accordance with an embodiment of the disclosure.

FIGS. 8A-B are SEM micrographs of TCP coating layers on Ti substrates fabricated using LENS™ at 500W power at a scan speed of 10 mm/sec. and with powder feed rate of (A) 9 g/min., and (B) 13 g/min. in accordance with an embodiment of the disclosure.

FIGS. 9A-B are interfacial SEM micrographs of TCP coating layers on Ti substrates fabricated using LENS™ at 500W power with powder feed rate of 13 g/min. and a scan speed of (A) 10 mm/sec., and (B) 15 mm/sec. in accordance with an embodiment of the disclosure.

DETAILED DESCRIPTION

Figure 1:
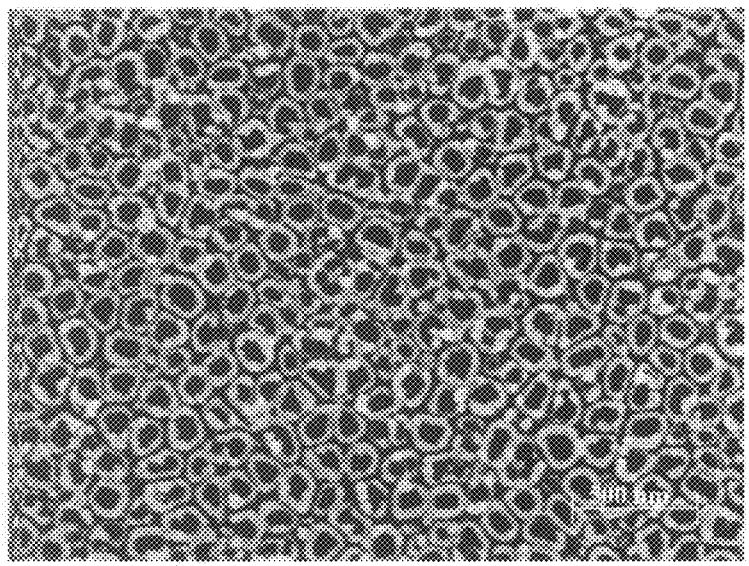
FIG. 1 is a FESEM image of nanoporous titanium oxide films anodized with an electrolyte-containing solution at 20V for 60 minutes in accordance with an embodiment of the disclosure.

The present disclosure describes embodiments and arrangements of metal surface modifications for improving interactions between natural bone cells and the implanted materials, and for improving antimicrobial and antifungal properties for metal-based implants. In some embodiments, surface modification of titanium (Ti) materials can negatively influence colonization of bacteria as well as promote interaction between human osteoblast cells and the modified implantable material. In one embodiment, Ti material surfaces can be oxidized to form a titanium dioxide (i.e., $TiO_2$, titania) layer on the Ti substrate. For example, anodization of Ti substrate surfaces can result in in situ titania formation in a porous form, or in another embodiment, a nonporous form. In some embodiments, the titania layers and/or porous nanostructures promote Human osteoblast (HOB) cell attachment and growth on the modified Ti substrate. In another embodiment, a laser engineered net shaping (LENS™) processing technique is described herein for coating metal implant surfaces (e.g., Ti surfaces) with uniformly distributed calcium phosphate-based bioceramics (or other calcium-based bioceramics) under optimized parameters to achieve a greater coating thickness. In a further embodiment, antimicrobial and/or antifungal particles can be deposited on the surfaces of the Ti material, a $TiO_2$ layer (e.g., a porous nanotube structure layer, a nonporous film, etc.), a calcium-based bioceramic coating layer, etc., to promote antimicrobial properties such as resistance to growth of Gram negative bacteria (e.g., *Pseudomonas aeruginosa*). In some embodiments, use of these surface treatment methods can be used to create coatings with composition gradients across the coating thickness, which can significantly reduce interfacial problems associated with a sharp interface that is typically present in conventional coating processes.

It will be appreciated that several of the details set forth below are provided to describe the following embodiments in a manner sufficient to enable a person skilled in the relevant art to make and use the disclosed embodiments. Several of the details and advantages described below, however, may not be necessary to practice certain embodiments of the disclosure. Additionally, the disclosure can include other embodiments that are within the scope of the claims but are not described in detail with respect to FIGS. 1-15.

A. Embodiments of Modified Metal Implant Materials and Methods for Preparing and Using such Materials In one aspect, the present disclosure is directed to methods for producing bone replacement materials with improved antimicrobial/antifungal properties and enhanced cellular adhesion (tissue integration), and to bone replacement materials produced therefrom. Surface modifications to enhance the interactions between bone cells and implant materials, e.g., Ti-based materials, are described herein. Some embodiments comprise surface coatings for Ti metal implants fabricated using both (1) electrochemical processing and/or anodization, and (2) laser processing, in order to enhance bone cell-materials interactions and achieve improved antimicrobial properties. In some embodiments, the surface treatment methods described herein can be applied as a post-processing operation to metallic implants such as hip, knee and spinal devices as well as screws, pins and plates.

Specific embodiments of suitable implant material compositions can include, but are not limited to; metals (e.g., titanium (commercially pure Ti, and both α and β alloys); aluminum (Al), iron (Fe), vanadium (V), etc.); metal alloys (e.g., Ti alloys with major alloying elements such as Al, V, Nb, Fe, Zr, Mo, O, Ni, Cr, Co; Ta forming alloys such as Ti6Al4V, Ti-6Al-7Nb, Ti-5Al-2.5Fe, Ti-12Mo-6Zr-2Fe, Ti-15Mo-5Zr-3Al, Ti-15Mo-3Nb-3O, Ti-13Nb-13Zr, Ti-35Nb-5Ta-7Zr; Stainless steel, CoCrMO, etc.), metal oxides (e.g., $TiO_2$); ceramics, inorganic salts (e.g., such as different forms of calcium phosphates and calcium carbonates and their combinations); polymeric materials and/or combinations thereof.

In one embodiment, modification of a metal implant surface (e.g., a Ti surface) includes fabrication of a $TiO_2$ surface layer for enhancing tissue integration. In some embodiments, the $TiO_2$ layer can be a porous layer having in situ titania nanotubes formed on a surface of a metal substrate. In other embodiments, the $TiO_2$ layer can be a nonporous film deposited on the metal substrate [16]. In one example, a $TiO_2$ layer having a thickness of approximately 50 nm or greater can positively influence natural bone cell behavior (attachment, spreading, proliferation, survival, etc.). $TiO_2$ can be deposited on a Ti surface using a variety of methods, such as thermal oxidation and electrochemical oxidation (e.g., anodization). In some arrangements, the primary composition of the porous or nonporous layer resulting from these methods includes $TiO_2$. In some embodiments, however, the composition can include small amounts of ions such as $Na^+$, $K^+$, $Mg^{2+}$, $Zn^{2+}$, $Sr^{2+}$, $Si^{2+}$, $Ca^{2+}$, or other metal ions, in a range of approximately 0-10 mol % of $TiO_2$.

In other embodiments, laser engineered net shaping (LENS™), which is a commercial, rapid prototyping (RP) process, can be used to coat a metal implant surface (e.g., a Ti surface) with uniformly distributed calcium phosphate (CaP). In one embodiment, the coating layer can include at least 60% of mixed phases of calcium phosphates, such as tricalcium phosphate (TCP), tetracalcium phosphate and hydroxyapatite. In some embodiments, the remainder of the coating layer can include a combination of base metal calcium phosphate compounds such as titanium phosphate, titanium oxide and calcium-titanium phosphate. In other embodiments the coating layer can include other resorbable ceramics, such as ceramics containing calcium phosphates (CaP), calcium sulfates (CaS) and calcium silicate (CaSi) compositions, alone or in combination, to improve the interactions between bone cells and implant materials. In another embodiment, phases of calcium phosphates incorporated in the coating layer can be in a crystalline form, an amorphous form, or a combination of crystalline and amorphous forms. Further, the composition of the coating layer can have a continuous concentration gradient from a metal substrate—coating interface to a coating surface (e.g., a low percentage of calcium-based bioceramic particles at the interface to a high percentage of calcium-based bioceramic particles at a coating surface).

TCP ($Ca_3(PO_4)_2$) is a CaP-based synthetic material that can form a bioactive bond with natural bone. Compared with hydroxylapatite, TCP has a lower calcium-to-phosphorous ratio, which can increase the degradation rate when the ceramic is placed in a biological environment, such as body fluid. TCP degrades in the body and the products are subsequently resorbed by the surrounding tissue. Therefore, such matrix absorption may be used to expose underlying surfaces to natural bone cells (e.g., osteoblast cells) or to release admixed materials such as antibiotics, growth factors (e.g., human growth factors, osteoinductive growth factors), or other biological agents (e.g., proteins, morphogens, pharmaceutical drugs, vitamins, etc.) in controlled drug release.

In one embodiment, compositions including CaP and CaSi can be useful for providing compositions having selectable controlled release profiles for bioactive agents, selectable controlled strength loss rates within a select period of time, etc. For example, mesoporous CaSi particles, such as those described in U.S. patent application Ser. No. 12/211,005 and which is incorporated in its entirety by reference, can be included in the coating layer for controlled release of bioactive agents. In some embodiments, a calcium-based composition for fabricating a bioceramic coating layer using LENS™ can include a Ca-based ceramic (e.g., CaP, CaS, CaSi) having at least one dopant included therein for providing selectable controlled strength loss rates. Examples of suitable dopants can include metal salts with metal ions (e.g., $Zn^{2+}$, $Mg^{2+}$, $Si^{2+}$, $Na^+$, $K^+$, $Sr^{2+}$, $Cu^{2+}$, $Fe^{3+}/Fe^{2+}$, $Ag^+$, $Ti^{4+}$, $CO_3^{2-}$, $F^-$), and in another embodiment, the dopant can include metal oxides (e.g., MgO, ZnO, NaF, KF, $FeO/Fe_2O_3$, SrO, CuO, $SiO_2$, $TiO_2$, $Ag_2O$ and $CaCO_3$).

In accordance with one embodiment of the disclosure, calcium-based bioceramic coatings (e.g., TCP, tetra-calcium phosphate, hydroxyapatite, CaSi, CaS, etc.) can be prepared on a commercially pure Ti (cp-Ti) substrate using a LENS™ system and technique. The LENS™ process can be used to coat the surface areas of metal implant materials with a high degree of accuracy, and desired physical and mechanical properties of the implant coating are attainable through appropriate selection of LENS™ process parameters (e.g., laser power, laser scan speed, bioceramic powder feed rate, etc.). In another embodiment, the bioceramic coating technique using LENS™ can also be used to repair a damaged coating due to its selectivity and precision. In some arrangements, a bioceramic composite coating layer can have a coating layer thickness of approximately 200 µm to approximately 700 µm. In other arrangements, the composite coating layer thickness can be between about 50 µm and about 900 µm, or from about 200 µm to about 400 µm. In further arrangements, the composite coating layer thickness can vary across a metal surface.

During the LENS™ coating process, a Nd:YAG laser can melt a surface of a Ti substrate (or other metal substrate). Simultaneously, calcium phosphate powder (or other calcium-based biocompatible ceramic powder) can be fed or delivered to the melted surface to mix with the molten metal and create a composite layer (e.g., a CaP—Ti composite layer). As laser power and/or powder feed rate increases, the thickness of the composite bioceramic coating can increase. In one embodiment, the volume of molten metal created due to laser heating can be a combined effect of laser power and interaction time between the laser and the material. For example, an increase in laser power (while other parameters are held constant) can transfer more heat energy to the substrate, which can increase the liquid-metal volume yielding a greater composite layer thickness. Similarly, an increase in laser scan speed can reduce the interaction time between the laser and the substrate thereby decreasing the amount of molten metal. Accordingly, the composite layer coating thickness can be increased or decreased as a function of laser scan speed.

In another embodiment, varying the powder feed rate while using LENS™ with a constant laser power and constant scan speed can yield varying composite bioceramic coating thicknesses even though the surface volume of liquid metal generated by the laser is substantially constant. For example, a decrease in powder feed rate can yield a significant decrease in composite coating thickness (e.g., about 100 µm). Similarly, a higher powder feed rate can be used to deliver more calcium-based bioceramic powder (e.g., TCP powder, HAp primary phase CaP powder, etc.) directly into the molten metal pool, increasing both the concentration of calcium-based bioceramic in the coating as well as increasing the total composite bioceramic coating thickness.

In a further embodiment, the volume fraction of calcium-based bioceramic in the coating can be strongly influenced by scan speed. Operation of the LENS™ laser at a slower scan speed can deliver more calcium-based bioceramic powder to the molten metal pool than operation at a faster scan speed. Moreover, higher interaction time (between laser and metal) at a slow scan speed can increase the volume of the molten metal pool on the substrate, which can then accommodate a proportionately greater amount of powder. Accordingly, calcium-based bioceramic (e.g., TCP, tetra-calcium phosphate, hydroxyapatite, CaSi, CaS, etc.) loading in the coating can increase with decreasing laser scan speeds.

In one embodiment, the coating layer includes one or more microstructures formed by the solidification of molten metal and bioceramic particles. In some embodiments, microstructure formation can vary within the composite coating layer created using the LENS™ process. For example, in coating regions closer to the composite coating-metal interface, the grain structures can have a columnar orientation. As the grain structures move along the thickness of the coating layer from the interface region to the exterior of the coating layer, the grain structures can transition to an equiaxed grain structure. Additionally, when a laser scan speed is reduced, a composite coating hardness value can correspondingly increase due to an increase in the volume fraction of calcium-based bioceramic in the coating.

In accordance with the present disclosure, embodiments of bioceramic composite coatings can provide improved biocompatibility between metal implants (e.g., Ti metal implants) and human osteoblast cells (HOB), by enabling cell attachment and proliferation. Further, embodiments of bioceramic composite coatings may also promote cell differentiation, extracellular matrix (ECM) formation and biomineralization.

In a further embodiment, antimicrobial and/or antifungal agents (e.g., silver, zinc oxide, aluminum oxide, copper oxide, and their combination, etc.) can be deposited on the surfaces of a metal implantable material, or a modified metal material having a $TiO_2$ layer (e.g., a porous nanotube structure layer, a nonporous film, etc.) and/or a calcium-based bioceramic coating layer to promote antimicrobial and antifungal properties. For example, a modified or non-modified Ti surface having a silver electroplated coat can effectively inhibit greater than 99% of *Pseudomonas aeruginosa* colony growth. Non-modified or modified Ti substrate surfaces without silver deposition do not demonstrate these inhibitory properties against colony formation and growth of *P. aeruginosa*.

In one embodiment, electrodeposition techniques can be used to deposit silver (Ag) on a titania nanotube surface, a $TiO_2$ nonporous film layer, a bioceramic composition coating, or other surface of a metal substrate to inhibit bacterial colony growth and/or fungal overgrowth. In one embodiment, a $TiO_2$ surface layer or a bioceramic composition coating, with or without silver deposits, can facilitate cellular attachment, high cell proliferation rates and enhanced bone cell-material interactions when compared to a non-modified Ti surface. Antimicrobial and/or antifungal agents can be deposited such that the deposits do not form a continuous coating on the metal surface, $TiO_2$ surface, calcium-based bioceramic composition coating, or other surface. For example, the antimicrobial and/or antifungal agents can be deposited, by any known deposition technique, in interconnected or particulate forms with particle sizes in the range of about 1 nm to about 100 microns.

In another embodiment, a metal device for attaching to bone includes a composite metal structure configured to be implanted in the body. The metal device can include a first surface region of the metal structure having titania nanotubes. The metal device can also include a calcium phosphate-based bioceramic surface coating on a second surface region of the composite metal structure. In a further embodiment, the first and/or second regions can have an antimicrobial and/or antifungal agent deposited thereon. In one arrangement, the first and second surface regions are separate regions. In another arrangement, the first surface region and the second surface region are at least partially overlapping. Another aspect of the disclosure is directed to a method for modifying a surface of a metal device for implanting in a body. The method can include oxidizing a metal surface of the device to form a $TiO_2$ layer, such as a porous layer having nanotube microstructures, or a non-porous layer having a titania film, on at least a portion of the surface. Following oxidation, the method can also include electrodepositing an antimicrobial and/or antifungal agent (e.g., silver) onto the metal surface of the device. Optionally, or in lieu of the oxidizing step, the method can include using a laser processing technique (e.g., LENS™) to coat one or more surface regions of the device with a calcium-based bioceramic surface coating. If desired, an antimicrobial and/or antifungal agent may be deposited onto the calcium-based bioceramic surface coating.

In a particular example, a hip joint implant can have a stem portion for inserting into a femur bone, a ball portion for replacing the head portion of the natural femur bone and a cup portion for replacing the patient's hip socket. The stem portion of the implant can be made of metal, such as titanium, having surface modifications for improving bone cell-materials interactions and/or inhibiting bacterial growth for diminishing risks related to post-surgical infection. In one embodiment, the stem portion could have single surface modification (e.g., titania nanotubes, silver deposition, bioceramic coating), or in other embodiments, the stem portion may include a combination of titania nanotube microstructure, silver deposition, bioceramic coating and/or other surface modification. Moreover, because the accuracy of the methods described herein, surface modifications and combinations of surface modifications can be in a complex pattern. Furthermore, the surface modifications described herein can be combined with other known modification used in the relevant art. In the example of a hip implant, the ball and socket portions may or may not include metal and may or may not include surface modifications. One of ordinary skill in the art will recognize other forms of implants that can have surface modifications, other body regions for attaching and/or inserting metal implants, as well as other attachment mechanisms (e.g., screws, pins, plates, etc.).

One of ordinary skill in the art will recognize that methods disclosed herein can be used to modify implantable metal devices having any size and shape. Furthermore, some embodiments of methods for modifying metal surfaces described herein may include modifying only a portion of the surface. Furthermore, implantable metal devices may include a first modified surface having a first modification and a second modified portion having a second modification. While sample sizes, shapes, and forms of implantable metal are disclosed herein in the context of examples, one of ordinary skill in the art will recognize other sizes, shapes and forms of samples that can be used as examples and/or as implantable metal devices.

B. Embodiments and Examples of Methods for Electrochemically Processing Surface Coatings on Ti Implants, and Characterization of Ti Metal Substrates Having Such Surface Modifications The following examples are intended to demonstrate aspects of the disclosure more fully without acting as a limitation upon the scope of the disclosure, as numerous modifications and variations will be apparent to those skilled in the relevant art.

In one embodiment, the surfaces of metal implantable materials, for example Ti metal materials, can be modified to enhance interactions between bone cells and the metal implantable materials as well as to increase antimicrobial properties for improving post-surgical healing and protecting the patient from postoperative infection.

Preparation of a Titania ($TiO_2$) Layer on Ti Surface

EXAMPLE 1

Commercially pure titanium (cp-Ti, 99.6% pure) sheets of 0.5 mm thickness were used as a starting material. In this example, circular Ti discs were cut having a 12 mm diameter and the samples were abraded with silicon carbide paper in successive grades from 600 to 1200 grit (Leco Corporation, MI) followed by ultrasonic cleaning in distilled water and air drying at room temperature. The Ti discs were then polished with a cotton polishing cloth using a 1 µm alumina suspension. Following the polishing step, the samples were anodized in a two-electrode electrochemical anodization cell, with a titanium anode and platinum cathode, and in an electrolytic aqueous solution containing approximately 0.1 mole/L sodium fluoride and approximately 1.0 mole/L of sulfuric acid at a constant dc voltage of 20V for about 60 minutes. During anodization, the electrolytic solution was stirred with a magnetic stir bar. Surface and lateral topography of the modified Ti samples was visualized using a field-emission scanning electron microscope (FESEM; FEI, Sirion, Oreg.) fitted with an energy dispersive spectroscopy (EDS) detector.

Anodization of Ti in the above-defined electrolytic aqueous solution containing sodium fluoride and sulfuric acid can result in a nanoporous morphology. FIG. 1 is a FESEM image of a cross-sectional view of nanoporous titanium oxide films anodized with the electrolyte-containing solution at 20V for 60 minutes in accordance with an embodiment of the disclosure. As shown in FIG. 1, examination of the cross-sectional view of the Ti substrate revealed the presence of nanotube structures. The average internal diameter of the nanotubes was 100 nm and the average length was 300 nm.

Nanotubes can be formed by two simultaneous processes: (1) an electrochemical etch, and (2) chemical dissolution [7, 8]. During electrochemical etching, an initial oxide layer forms on a Ti surface due to the interaction between $Ti^{4+}$ and $O^{2-}$ ions. In the presence of $F^-$ ions, oxide layers dissolve partially and nanometer sized pits are formed. At the base of the pits, both chemical dissolution and electrochemical etching can take place to form a thin barrier layer, which can increase the electric-field intensity resulting in further pore growth. As the barrier layer decreases, and higher electric field intensity causes further electrochemical oxidation and dissolution, separate channels are formed and give rise to the final nanotube structure shown in FIG. 1.

The specific electrolyte composition chemistry described in Example 1 was chosen following experimentation using a plurality of electrolyte compositions [9]. As a result of such experimentation, the inventors found that two specific electrolyte criteria are desirable for forming nanoporous morphology: (1) the presence of fluoride ions, and (2) acidic solutions. Sodium fluoride (NaF) completely dissociates in water yielding $F^-$ ions to form HF and $OH^-$ ions. HF is a weak acid in an acidic solution with a dissociation constant ($K_{a1}$) of $6.8*10^{-4}$ which is low in comparison to strong acids like $H_2SO_4$ which has a second dissociation constant ($K_{a2}$) of $1.2*10^{-2}$, or $H_3PO_4$ which has a third dissociation constant ($K_{a3}$) of $7.5*10^{-3}$. Because most of the $F^-$ ions exist in the form of HF, the presence of strong acids in the electrolytic solution prevents HF from dissociation, thus inhibiting high chemical dissolution and thereby allowing the nanotube array structure to be maintained. One of ordinary skill in the art will recognize other electrolyte solutions for forming nanotube microstructures as well as additional anodization conditions and arrangements.

Electrodeposition of Silver

In another embodiment, silver (Ag) can be electrically deposited onto the surface of Ti.

EXAMPLE 2

Figure 2A:
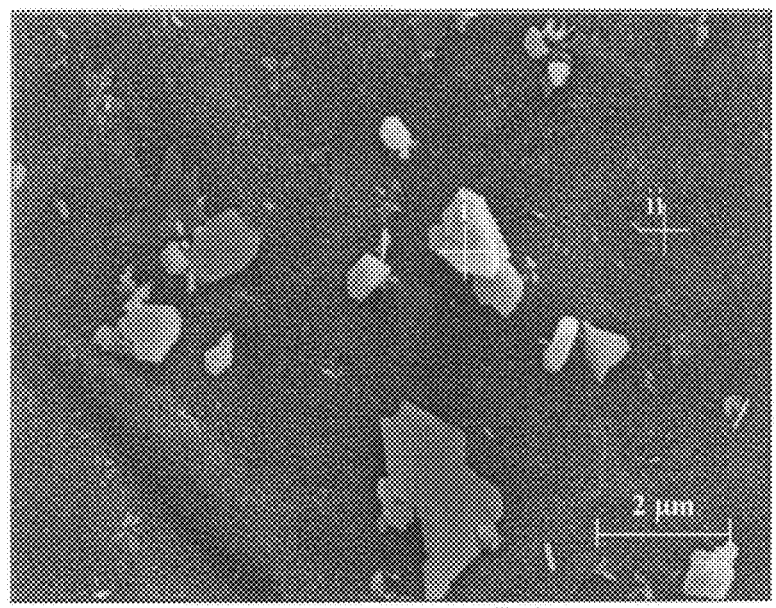
FIGS. 2A-C are, respectively, (A) a FESEM image of a silver coated nanoporous titanium oxide film surface, (B) a graphical representation of an EDS analysis of the elemental silver deposited on the Ti surface marked at (i) in FIG. 2A, and (C) a graphical representation of an EDS analysis of a nanoporous surface region having minimal silver deposition marked at (ii) in FIG. 2A in accordance with an embodiment of the disclosure.
Figure 2B:
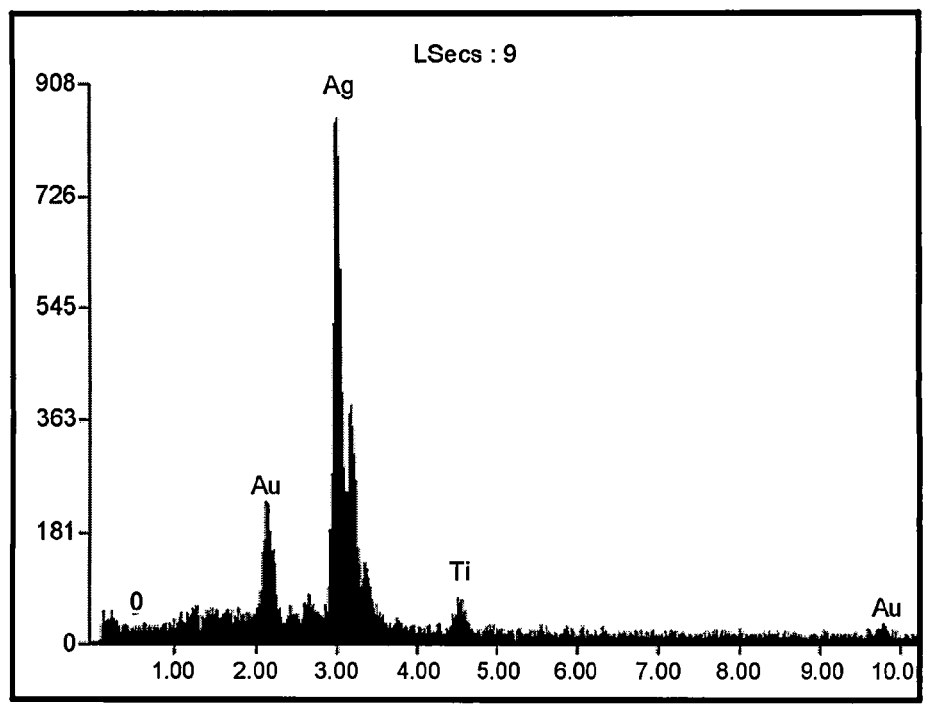
Figure 2C:
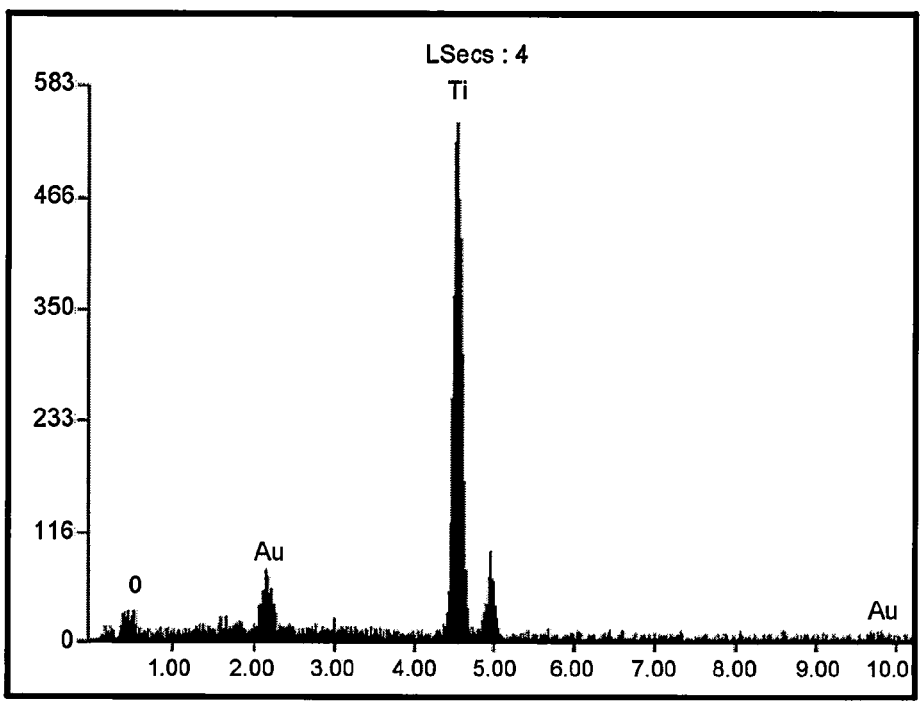

In a specific example described herein for purposes of illustration and in accordance with an embodiment of the disclosure, six anodized samples were cleaned and anodized a second time with approximately 0.01 M silver nitrate solutions at 5V for about 2 minutes to produce silver deposited Ti samples. In this example, the silver deposited samples are denoted as Ag-1, Ag-2, Ag-3, Ag-4, Ag-5 and Ag-6. Anodized Ti samples without silver deposition (e.g., control samples) are referenced as C-1, C-2, C-3, C-4, C-5 and C-6. FIGS. 2A-C are, respectively, (A) a FESEM image of a silver coated nanoporous titanium oxide film surface, (B) a graphical representation of an EDS analysis of the elemental silver deposited on the Ti surface marked at (i) in FIG. 2A, and (C) a graphical representation of an EDS analysis of a nanoporous surface region having minimal silver deposition marked at (ii) in FIG. 2A in accordance with an embodiment of the disclosure. As shown in FIG. 2B, the samples anodized with the silver nitrate solution demonstrate the presence of elemental silver on the nanoporous titania surface. As shown in FIG. 2C, in regions of the nanotube titania surface not covered by elemental silver deposits, elemental Ti and O are visible.

Bone Cell-materials Interactions

Interactions between natural bone cells and the metal implant materials can be characterized with in vitro biocompatibility assessments using a human osteoblast (HOB) cell line. HOB cells can be derived from an osteoblastic precursor cell line (OPC1) established from human fetal bone tissue.

EXAMPLE 3

In this example, cells were plated at a density of approximately $10^5/cm^2$ in 100 mm tissue culture plates and cultured in McCoy's 5A medium (with L-glutamine, without phenol red and sodium bicarbonate) and supplemented with 5% fetal calf serum (FCS), 5% bovine calf serum (BCS), 2.2 gm/liter sodium carbonate, 100 mg/liter streptomycin, and 8 □g/ml Fungizone (Gibco™ Laboratories, Grand Island, N.Y.). Cells were maintained at 37° C. under an atmosphere of 5% $CO_2$ and 95% air.

To examine the interactions between bone cells (e.g., OPC1 cells) and a nanoporous titania surface, anodized nanoporous $TiO_2$ samples with and without a silver coating, as described in Examples 1 and 2 above, were autoclaved at about 121° C. for 45 minutes. Following the autoclaving step, OPC1 cells were seeded from the cultured plate to a top surface of the autoclaved samples in new culture plates. For example, OPC1 cells were cultured on a series of control nanoporous surfaces (C-series described above) and on a series of silver-coated nanoporous surfaces (Ag-series described above). The cell-seeded samples were maintained at 37° C. under an atmosphere of 5% $CO_2$ and 95% air. Culture media was changed every two days for all culture sample plates. In the example described herein, all OPC1 cells originated from the same cell line passage and all plates were kept under identical conditions.

The OPC1 cells were cultured with the C-series and Ag-series samples for either 5 or 11 days before the samples were fixed. The samples were fixed with 2% paraformaldehyde/2% glutaraldehyde in 0.1 M cacodylate overnight at 4° C. Following a rinse in 0.1 M PBS, each sample was fixed in 2% osmium tetroxide ($OsO_4$) for two hours at room temperature. Following the fixation steps, the samples were rinsed with 0.1M cacodylate and dehydrated using an ethanol (EtOH) series for 10 minutes each. Bone cell-materials interactions were evaluated for each of the fixed samples using scanning electron microscopy (SEM Hitachi's 570).

Figure 3A:
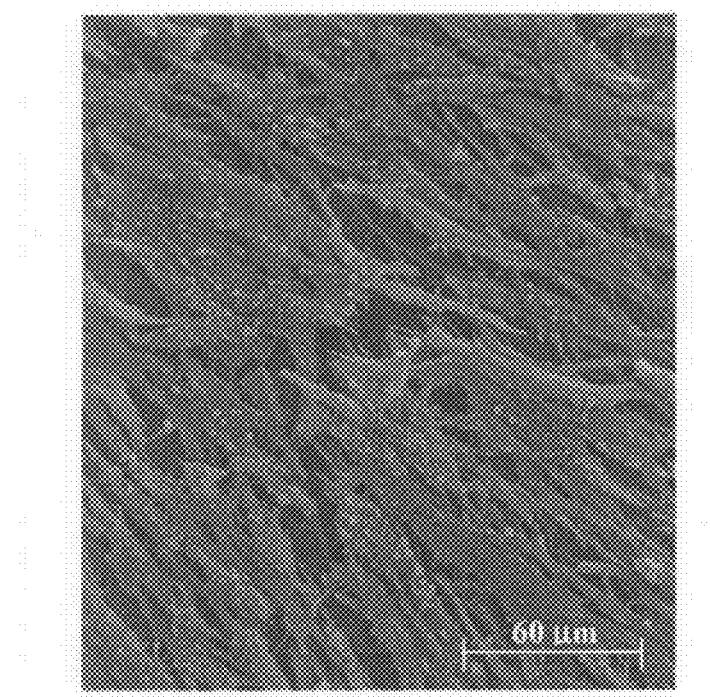
FIGS. 3A-B are, respectively, SEM micrographs of OPC1 cell morphology on a (A) nanoporous control surface, and (B) a silver-coated nanoporous surface after 11 days of cell incubation in accordance with an embodiment of the disclosure.
Figure 3B:
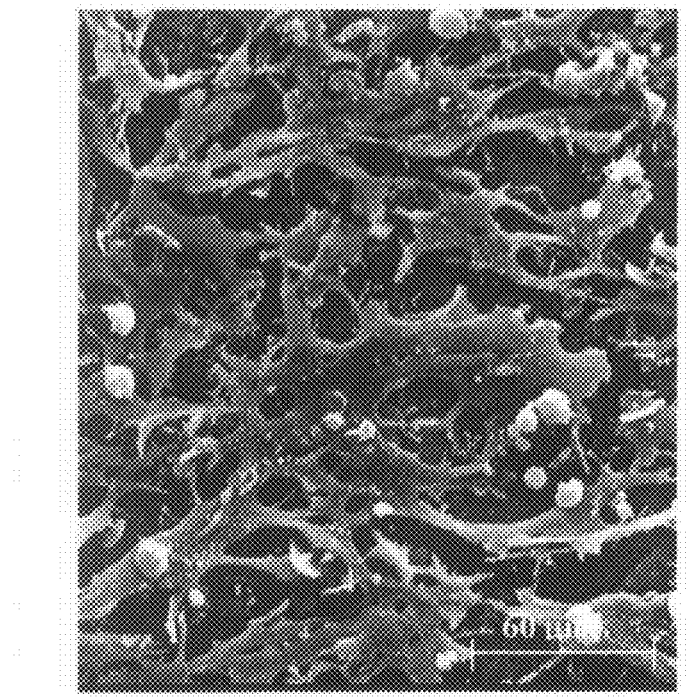

FIGS. 3A-B are, respectively, SEM micrographs of OPC1 cell morphology on a (A) nanoporous control surface, and (B) a silver-coated nanoporous surface after 11 days of cell incubation in accordance with an embodiment of the disclosure. In both samples, the OPC1 cells demonstrate a filamentous network structure with cell-cell attachment and cell spreading along the nanoporous surface. As shown in FIG. 3A, nodule formation was pronounced on nanoporous surfaces indicating early cell differentiation during 11 days in cell culture. As shown in FIG. 3B, cell morphology on silver-coated samples (Ag-series) demonstrates that the number of interactions between OPC1 cells and the surface-treated material were diminished when compared to the nanoporous surface (C-series) without a silver coating. As demonstrated in this example, silver deposition decreased the amount of cell-material interaction; however, this observation is not attributed to cell death. In this example, no cell death was documented for the samples (C-series or Ag-series) incubated over 5 days or 11 days. Therefore, no adverse toxicity effects were observed due to the Ag-coating on the sample surfaces.

Cell Proliferation

Cell proliferation can also be considered in a determination of metal implant material in vitro biocompatibility.

EXAMPLE 4

In this example, OPC1 cell proliferation on either Ti control samples (3 samples each of Ag-coated [Ag—Ti] and non-coated [Ti]) or nanoporous Ti surfaces (3 samples each from the C-series and Ag-series) were evaluated using a 3-(4, 5-dimethylthiazol-2-yl)-2,5-diphenyl tetrazolium bromide (MTT) assay. MTT (Sigma, St. Louis, Mo.) solution at 5 mg/ml was prepared by dissolving MTT in PBS followed by filter sterilization. The MTT solution was then diluted by transferring 50 □l of the sterile concentrated solution into 450 □l of serum free phenol red-free Dulbeco's minimum essential (DME) medium, which was then transferred into each of the test wells (each containing an anodized Ti sample) of a 12-well tissue culture plate for the cell proliferation assay. During the MTT assay, cellular metabolic activity can convert the tetrazolium in the MTT solution to formazan products. In this example, formazan formation was allowed to proceed for 2 hours at 37° C. The level of cellular metabolic activity was determined by extracting the formazan products in 500 □l of a solubilization solution (10% triton X-100, 0.1N HCl and isopropanol). Following extraction, 100 □l of the solubilization solution was transferred to a fresh 96 well plate and the optical density of the solution in each well was measured at a wavelength of 570 nm using a Microplate reader (Cambridge Tech. Inc., Model 700 EIA). The data was presented as a mean optical density value with a standard deviation for each sample.

Figure 4:
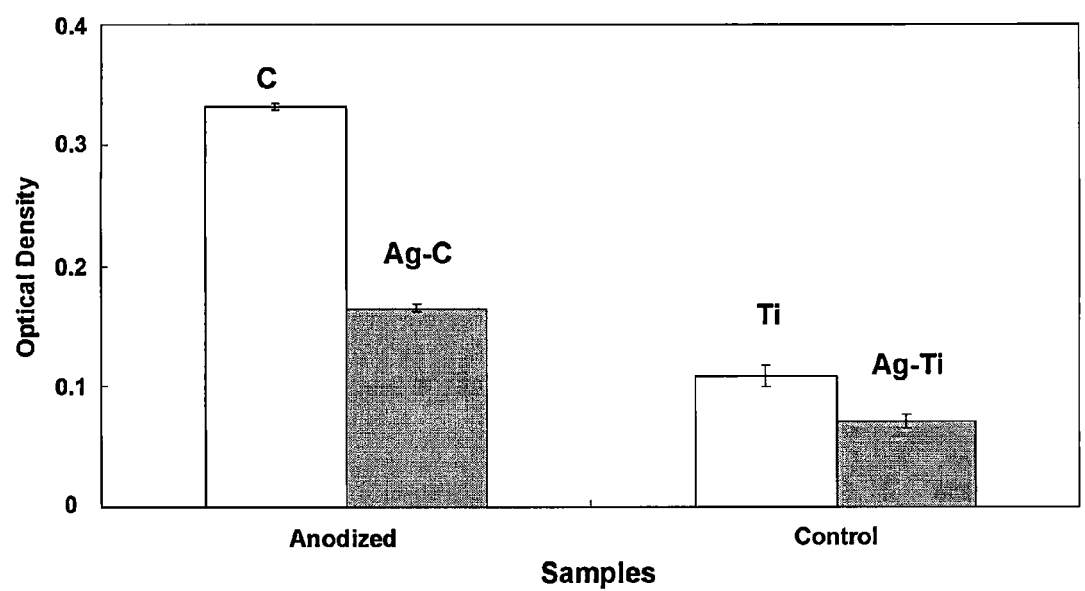
FIG. 4 is a graphical representation of optical density measured at a wavelength of 570 nm by a microplate reader following OPC1 cell culture incubation with silver electroplated and non-electroplated nanoporous Ti samples for 11 days in accordance with an embodiment of the disclosure.

FIG. 4 is a graphical representation of the optical density of the extracted formazan products measured at a wavelength of 570 nm by a microplate reader following OPC1 cell culture incubation with the anodized and non-anodized Ti samples with and without silver electroplated surfaces for 11 days in accordance with an embodiment of the disclosure. As shown in FIG. 4, silver electrodeposited samples, Ag-series and Ag—Ti, showed lower cell density, and therefore reduced cellular proliferation, when compared to the samples without silver electroplating, C-series and Ti, respectively. Moreover, nanoporous surfaces (Anodized) showed higher cell density, and therefore increased cellular proliferation, in comparison to the non-nanoporous (Control) samples for both silver deposited and non-silver coated samples.

Antimicrobial Tests

As noted above, bacterial infection and/or fungal overgrowth can be a side effect often associated with implants and bone replacement surgeries.

EXAMPLE 5

In this example, bacterial growth tests using the Gram-negative bacteria, *Pseudomonas aeruginosa* (ATCC 9027) was used to assess antimicrobial properties associated with the modified metallic implant substrates of Examples 1 and 2 described above. The bacterial growth tests described in this example were conducted using *P. aeruginosa* because approximately 80% of infections associated with metallic implants are caused by Gram-negative bacteria.

In this example, 12 mm discs of silver-coated anodized Ti substrates (Ag-series) and anodized Ti substrates without silver (C-series) were placed into individual wells of sterile tissue culture plates. The samples were then challenged with a volume to surface area ratio of 0.6 ml bacterial inoculum/$cm^2$. For example, to each well containing the Ti samples, 1.2 ml of inoculum prepared in M101 medium (see Table 1) and containing ~$1 \times 10^5$ colony forming units (cfu) of *P. aeruginosa* were added. The inoculum was prepared by diluting an overnight broth culture of *P. aeruginosa* in M101 medium to yield an initial inoculum of ~$1 \times 10^5$ cfu/ml. The multi-well plate was then covered with a sterile lid and incubated at 37° C. for 24 hours. Following incubation, the supernatant fluid from each well was appropriately diluted and plated on Trypticase soy agar (TSA) plates. The plates were then incubated at 37° C. for 24 hours and surviving colony-forming bacteria were counted. The log reduction resulting from modified Ti substrates was calculated by subtracting the log survivors of the test wells from the log survivors of control wells (e.g., unmodified Ti substrates).

TABLE 1

Components of the M101 Challenge Medium

| Component A | Grams per liter | Component B | Grams per Liter |
|---|---|---|---|
| Sodium citrate | 1.3 | Calcium Chloride | 1.3 |
| Potassium phosphate | 1.3 | Magnesium chloride | 1.3 |
| Sodium oxalate | 2.0 | Sodium chloride | 9.8 |
| Urea | 25.0 | Sodium sulfate | 4.6 |
| | | Potassium Chloride | 3.2 |
| | | Ammonium chloride | 2.0 |
| | | Urea | 25.0 |

Sterilize each solution and then combine at equal parts for use.

Table 2 shows results of antimicrobial activity for three bacterial dilution levels following a 24 hour incubation period. Referring to Table 2, the C-series samples demonstrated no antimicrobial effects as evidenced by the high number of surviving bacterial colonies in each C-series well. In contrast, each well containing an Ag-coated 12 mm diameter disk sample (e.g., Ag-1 to Ag-6) demonstrated superior antimicrobial properties when compared to the non-coated samples For example, only one Ag-coated sample (Ag-1) had surviving colonies (e.g., 30 colonies; average: 30/3=10 colonies) while the assay plating results from the remaining Ag-coated samples were devoid of colonies. Therefore, log reduction in bacteria colony forming units (cfu) due to the silver coating on modified Ti disk substrates can be estimated as the logarithm of the ratio of initial bacterial cfu to the average number of final surviving colonies. The resultant value in this example was 4.94 (i.e., log ratio reduction >4 equates to approximately a >99.99% reduction in bacteria), demonstrating a very strong antimicrobial efficacy for the silver-coated substrates. In contrast, control nanotube Ti samples (C-series) demonstrated no antimicrobial properties compared to bacterial growth in medium alone as indicated by a comparable surviving bacterial count at the $1 \times 10^{-5}$ dilution level in the C-series samples and in the medium alone.

TABLE 2

Results of the antibacterial capacity of Ag electrodeposited samples
against the growth of bacterial colonies after 24 hours

| Test Sample | 0 time count cfu/ml | Dilution 1 × 10⁻¹ | Dilution 1 × 10⁻³ | Dilution 1 × 10⁻⁵ |
|---|---|---|---|---|
| | | 24 h count | | |
| Ag-1 | $8.9 \times 10^5$ | 3 | 0 | 0 |
| Ag-2 | $8.9 \times 10^5$ | 0 | 0 | 0 |
| Ag-3 | $8.9 \times 10^5$ | 0 | 0 | 0 |
| Ag-4 | $8.9 \times 10^5$ | 0 | 0 | 0 |
| Ag-5 | $8.9 \times 10^5$ | 0 | 0 | 0 |
| Ag-6 | $8.9 \times 10^5$ | 0 | 0 | 0 |
| C-1 | $8.9 \times 10^5$ | TMTC* | TMTC | 1064 |
| C-2 | $8.9 \times 10^5$ | TMTC | TMTC | 976 |
| C-3 | $8.9 \times 10^5$ | TMTC | TMTC | 1248 |
| C-4 | $8.9 \times 10^5$ | TMTC | TMTC | 1016 |
| C-5 | $8.9 \times 10^5$ | TMTC | TMTC | 1288 |
| C-6 | $8.9 \times 10^5$ | TMTC | TMTC | 1216 |
| Medium | $8.9 \times 10^5$ | TMTC | TMTC | 1236 |
| Medium | $8.9 \times 10^5$ | TMTC | TMTC | 1128 |

*The zero time plate count was $8.9 \times 10^8$ cfu/mL, TMTC = Too Many To Count Two possible explanations for the observed antimicrobial properties of Ag can be that (1) the silver metal can react with water and release silver ions which may then combine with sulphydryl groups of respiratory enzymes or nucleic acids in the bacteria, resulting in a respiratory block and ultimately causing death of the bacterium [10], and (2) silver may react with the oxygen dissolved in the medium and generate activated oxygen O* which may decompose the bacterium [11-14].

The results demonstrated in the above Examples show that Ti substrate surfaces can be modified by formation of titania nanotubes to enhance interactions between bone cell and implantable metal materials. Further, the nanoporous surface can be silver-coated to enhance antimicrobial properties on the surfaces of the implantable materials. Accordingly, the results from the examples described above confirm that surface modification can improve both osseointegration and reduce chances of infection, which are advantageous properties for metallic devices that can be used for a variety of biomedical applications including metal implants.

C. Embodiments and Examples of Methods for Laser Processing of Surface Coatings on Ti Implants and Characterization of Ti Metal Substrates Having Such Surface Modifications Overview of a LENS™ Processing for Improving Biocompatibility Compounds having bioresorbable properties encourage bone growth and facilitate integration with bone tissue. Both in vitro and in vivo studies have shown that bioactive calcium phosphate-based ceramics are biocompatible and osteoconductive; however, these ceramic materials are brittle in nature and can only be used as a coating or as bone fillers. The usefulness of a coated implant depends on the stability of the coating which is governed by its physical and mechanical properties. One aspect that is useful to address for any coated implant is the long term adherence of the coating with the substrate. A coating which separates from the implant in vivo would provide no advantage over an uncoated implant and the resultant debris material from the coat separation can render these coating systems even less desirable for use within the body. A variety of different techniques have been used to coat metallic implants with calcium phosphate-based ceramics such as, for example, dip coating, sol-gel, electrophoretic deposition, biomimetic coating, simultaneous vapor deposition, pulsed laser deposition and plasma spraying. The success of these coating processes can depend on the ability to achieve high crystallinity within the coatings, good adherence between the ceramic and the metal, control over coating thickness and the ability to coat porous and complex shapes. Among them, an electrophoretic deposition process has been most widely used to coat porous and complex shaped implants. However, high temperature sintering of such electrophoretically deposited coatings can often lead to cracking at the substrate-coating interface.

Dip coating and sol-gel processes are good for getting a thin coating on implants, but achieving a thicker coating is often very difficult. Plasma spray calcium phosphate-based ceramic coatings suffer from low crystallinity and poor interfacial bonding. In addition, a high cooling rate can introduce cracks in the coatings which can reduce the adhesion strength between the substrate and the coated ceramic.

Bioactive calcium phosphate-based ceramics, especially hydroxyapatite (HAp) and tricalcium phosphate (TCP), have chemical and crystallographic similarity to natural bone. TCP may have applicability in bone reconstruction and remodeling due to its bioresorbable properties, ready availability and controlled size variation. Among these applications, coating on metallic implants can improve tissue integration of the coated implants by providing a bioactive surface on otherwise bioinert material, which can improve healing time. Examples of such coatings can be found in International Publication No. WO/2007/124511, U.S. Publication No. 2007/0203584 A1 and U.S. patent application Ser. No. 12/211,005, each of which is incorporated in their entirety by reference.

In accordance with one embodiment of the disclosure described herein, TCP coatings can be prepared on a commercially pure Ti (cp-Ti) substrate using LENS™, a laser engineered net shaping and rapid prototyping (RP) process. TCP can be used as a representative material from the calcium phosphate family of bioceramics for which 45-150 micron size powders, desirable for LENS™ processing, can be readily available. However, this process can be easily extended to other calcium phosphate, calcium silicate and calcium sulfate-based materials.

Figure 5:
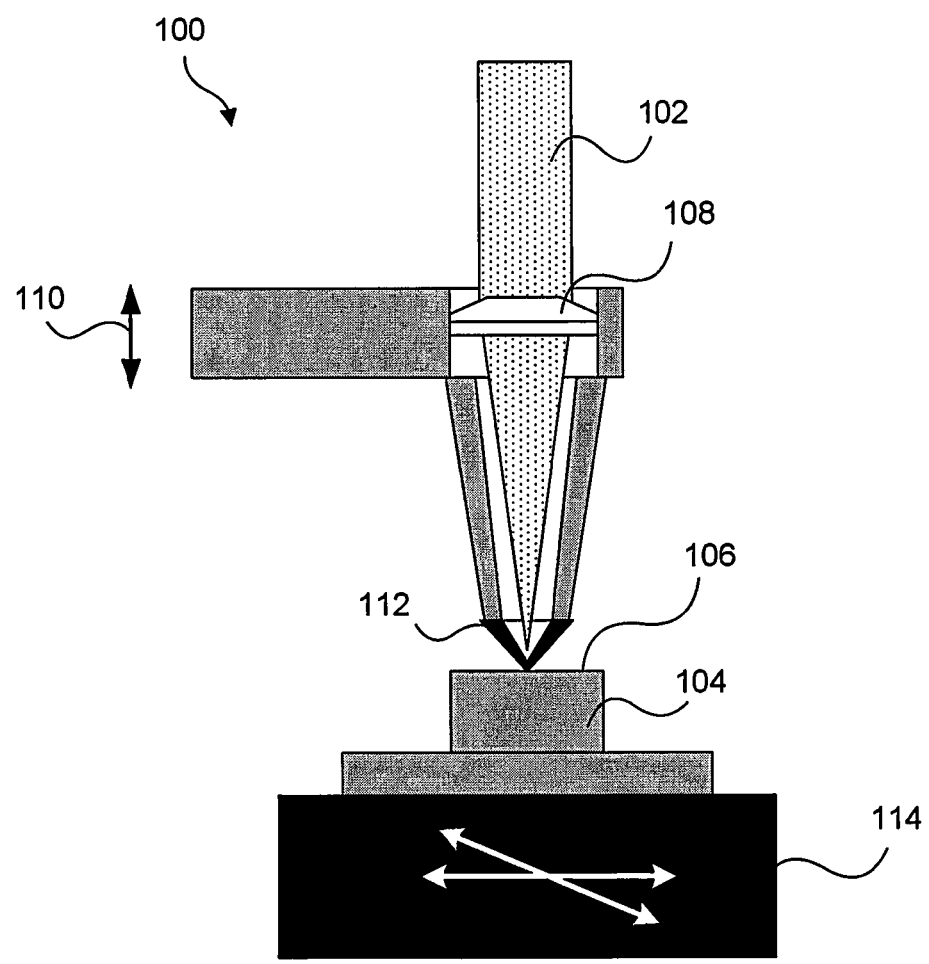
FIG. 5 is a schematic representation of a LENS™ processing device in accordance with an embodiment of the disclosure.

Laser beams, owing to their high coherence and directionality, have the ability to locally melt the surface of a metal substrate. A schematic representation of the LENS™ processing device 100 is shown in FIG. 5. The device can include a Nd:YAG (neodymium-doped yttrium aluminum garnet) laser that can have laser power 102 focused onto a metal substrate 104 to create a molten metal pool on the substrate surface 106. The laser beam 102 can be focused on the substrate surface 106 by moving one or more focusing lenses 108 along a Z-positioning axis 110. Powder (e.g., calcium phosphate powder) can then be injected into the metal pool from one or more powder delivery nozzles 112 associated with the LENS™ processing device 100. As the molten metal cools, the composite bioceramic powder-metal composite later subsequently solidifies. The substrate 104 can then be scanned relative to the deposition head to a write line of the metal having a finite width and thickness. Back and forth rastering (e.g., using an X-Y positioning stage 114) can create a pattern with fill material (e.g., powder) in a desired area to allow a layer of material to be deposited. This procedure can be repeated several times until an entire solid or tailored porosity volumetric coverage (e.g., as represented in a three-dimensional CAD model) is produced on the substrate 104. In some arrangements described below, LENS™ can be used for surface treatments of metals in which ceramic powder can be fed into a laser-generated molten metal pool to form a metal-ceramic composite. In one embodiment, a 0.5 kW continuous wave Nd:YAG laser beam can be used to coat TCP particles on cp-Ti.

Calcium Phosphate Coating

EXAMPLE 6

In this example, commercial grade calcium phosphate powder with HAp as a primary phase (Monsanto, CA) having a particle size ranging from 45 to 150 μm was used to coat a 0.89 mm thick Ti substrate (Alfa Asear) of 99.7% purity. Average specific surface area of the precursor powder was determined by the Brunauer, Emmett and Teller (BET) method (5 point analyzer, Tristar Micromeritics, USA) after degassing at 350° C. with a continuous flow of nitrogen. The Ti substrate was cleaned with acetone to remove organic materials from the surface prior to coating. A LENS 750 (Optomec, Albuquerque, N. Mex., USA) unit with a 0.5 kW continuous wave Nd:YAG laser was used to coat Ti substrates. During laser fabrication, the top surface of the Ti metal substrate was melted and TCP powder was fed to the molten metal region with the help of a carrier gas (e.g., Argon). The molten metal, along with the trapped TCP powder, solidified rapidly as the laser head moves across the substrate. To reduce the oxidation of Ti, the coatings were fabricated in a controlled atmosphere with total $O_2$ content less than 10 parts per million (ppm) in an atmospheric chamber.

Laser power, scan speed and powder feed rate can be varied during synthesis of the coatings. Specific examples of LENS™ parameters that can be used are listed in Table 3. In some examples described below, Ti substrates were coated with TCP using 400W or 500W laser power (energy density of the laser beam can be 224 W/mm$^2$ and 280 W/mm$^2$, respectively) and with a scan speed of 10 mm/sec. or 15 mm/sec. In some examples, powder feed rates of 9 g/min. or 13 g/min. were used. One of ordinary skill in the art will recognize that the parameters presented in Table 3 are exemplary, and that different parameter settings can be selected, e.g., such as settings based on prior optimization for processing desirable coating characteristics. In one embodiment, single layer TCP coatings can be synthesized; however, the scanning/coating process may be repeated many times according to the design requirement.

TABLE 3

Processing parameters used to fabricate TCP coatings

| | LENS ™ Parameters | | |
|---|---|---|---|
| Coating | Laser Power | Laser Scan Speed | Powder Feed Rate |
| Single Layer | 400 W or 500 W | 10 nm/sec. or 15 nm/sec. | 9 g/min. or 13 g/min. |

Characterization of TCP Coatings on Ti Substrates

EXAMPLE 7

To analyze the coated Ti products of Example 5, the coated samples were cross-sectioned, mounted and prepared for metallographic observation. In this example, top surfaces of the coatings were polished to observe the distribution of TCP in the coating. The polished sections were etched with a solution of hydrofluoric acid (49% by acidometry), nitric acid (15.8 N) and distilled water in a ratio of 1:2:25 to reveal coating microstructure. Microstructural characterization of the top and cross-sectioned surfaces of the coating was performed using a scanning electron microscope (Hitachi s-570 SEM). Siemens D500 Krystalloflex X-ray diffractometer using copper Kα radiation at 30 kV was used to determine different phases in the coating. Energy dispersive spectroscopy (EDS) was also used for qualitative chemical microanalysis of the coating surface. Further, Vicker's microhardness (Leco, M-400G3) measurements were carried out on transverse sections of the coating by applying a 200 gm load for 10 seconds, and an average of 5 measurements on each sample are reported.

Coating Thickness

In the examples described below, the thickness of the TCP coating was found to be influenced by laser power, scan speed and powder feed rate.

EXAMPLE 8

FIGS. 6A-B are SEM micrographs of TCP coating layers on Ti substrates fabricated using LENS™ at a scan speed of 15 mm/sec. with a powder feed rate of 13 g/min. and at (A) 500 W laser power, and (B) 400 W laser power in accordance with an embodiment of the disclosure. The cross-sectional micrographs of TCP coatings shown in FIGS. 6A-B indicate variations of coating thickness with varying laser power. For example, the coating thickness increased from 250 μm to 400 μm when the laser power was increased from 400 W to 500 W.

EXAMPLE 9

Figure 7A:
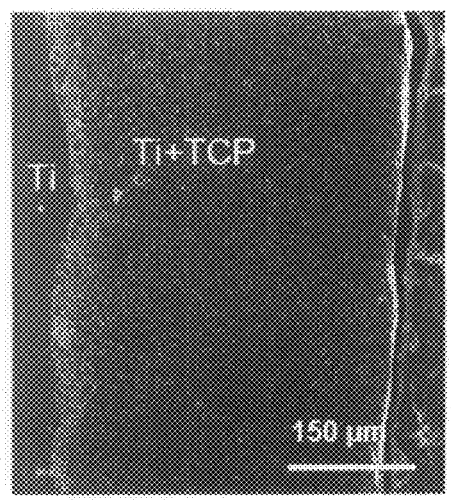
FIGS. 7A-B are SEM micrographs of TCP coating layers on Ti substrates fabricated using LENS™ at 500W power with a powder feed rate of 14 g/min. and a scan speed of (A) 10 mm/sec., and (B) 15 mm/sec. in accordance with an embodiment of the disclosure.
Figure 7B:
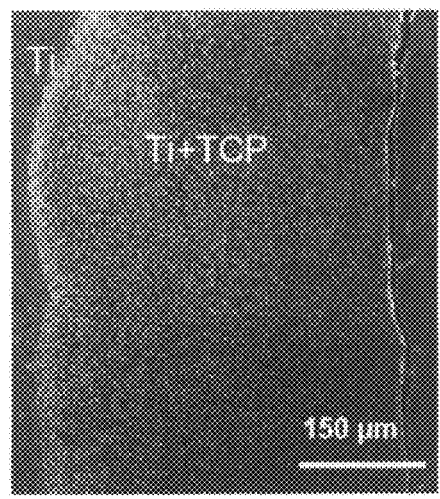

In this example, the thickness of the TCP coating was found to be influenced by laser scan speed. FIGS. 7A-B are SEM micrographs of TCP coating layers on Ti substrates fabricated using LENS™ at 500 W power with a powder feed rate of 14g/min. and a scan speed of (A) 10 mm/sec., and (B) 15 mm/sec. in accordance with an embodiment of the disclosure. Increasing the scan speed from 10 mm/sec. to 15 mm/sec. while keeping the laser power at a constant de voltage of 500W resulted in a decrease of the coating thickness by a range of about 60-80 μm. However, the coating was uniform with respect to TCP distribution and concentration over the entire region.

EXAMPLE 10

In this example, the thickness of the TCP coating was also found to be influenced by TCP powder feed rate. FIGS. 8A-B are SEM micrographs of TCP coating layers on Ti substrates fabricated using LENS™ at 500 W power at a scan speed of 10 mm/sec. and with powder feed rate of (A) 9 g/min., and (B) 13 g/min. in accordance with an embodiment of the disclosure. As shown in FIGS. 8A-B, the thickness of the coating decreased by approximately 100 μm when the powder feed rate was decreased from 13 g/min. to 9 g/min.

Microstructure and Volume Fraction of TCP

EXAMPLE 11

In one embodiment, the loading of TCP particles in the coating can also be significantly affected by a combination of laser scan speed and powder feed rate. FIGS. 9A-B are interfacial SEM micrographs of TCP coating layers on Ti substrates fabricated using LENS™ at 500 W power with a powder feed rate of 13 g/min. and a scan speed of (A) 10 mm/sec., and (B) 15 mm/sec. in accordance with an embodiment of the disclosure. At a slower scan speed (shown in FIG. 9A), a higher volume fraction of TCP was observed in the coatings compared to coatings made at a higher scan speed (see FIG. 9B).

EXAMPLE 12

Figure 10A:
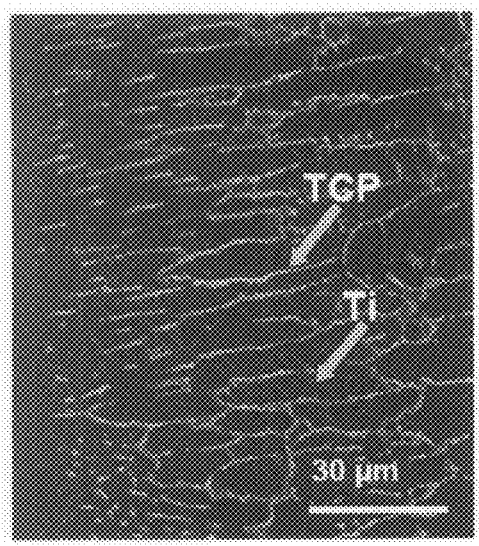
FIGS. 10A-B are SEM micrographs of the microstructure of TCP coating layers on modified Ti substrates fabricated using LEN™ at 500W power, 10 mm/sec. scan speed and 9 g/min. powder feed rate and showing a composite layer region (A) close to the metal substrate, and (B) along an exterior surface of the coating layer in accordance with an embodiment of the disclosure.
Figure 10B:
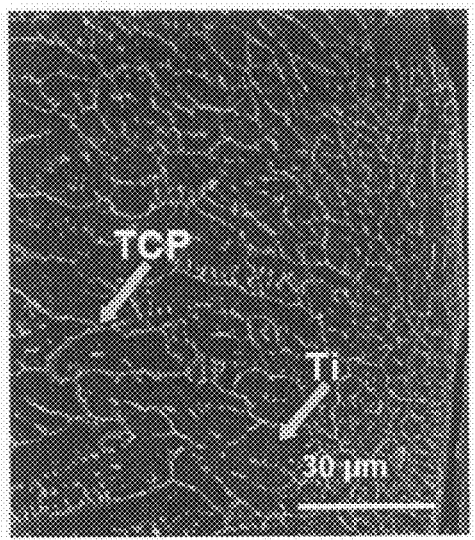

FIGS. 10A-B are SEM micrographs of cross-sections of the microstructure of TCP coating layers on modified Ti substrates fabricated using LENS™ at 500 W power, 10 mm/sec. scan speed and 9 g/min. powder feed rate and showing a composite coating layer region (A) close to the metal substrate, and (B) along an exterior surface of the coating layer in accordance with an embodiment of the disclosure. Referring to FIGS. 10A-10B, within the metal-bioceramic composite layer, the microstructure changes from columnar Ti grains at the lower region of the composite layer to equiaxed grains near the exterior surface of the composite layer. The lower region of the coating layer (e.g., closest to the metal substrate) shows columnar grain growth of Ti with TCP particles along the grain boundaries (shown in FIG. 10A). Moreover, the interface between the composite coating layer and the metal substrate appears diffused. FIG. 10B shows the equiaxed grains at and near the exterior surface of the composite coating layer. In this region the TCP particles were found to align along the grain boundaries. Moreover, the volume fraction of TCP in this region was greater when compared to the lower region nearest the metal substrate. The variation of grain structure is primarily due to the concentration of TCP during solidification of Ti.

EXAMPLE 13

Figure 11:
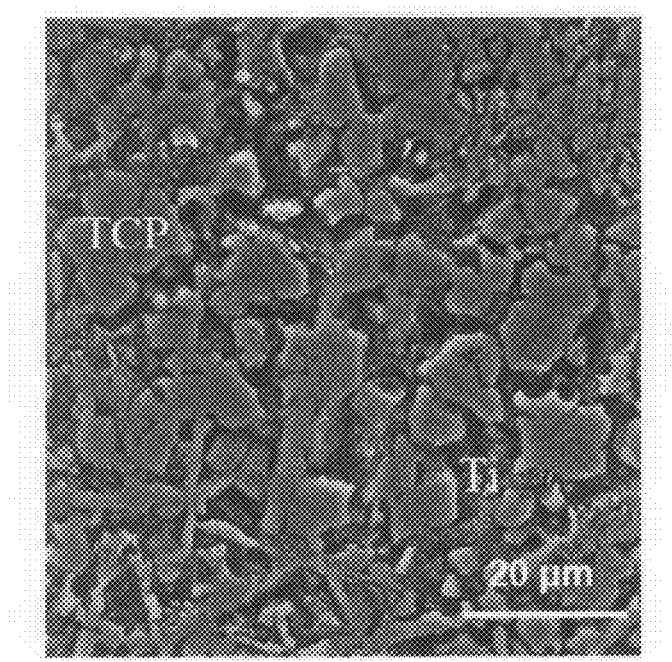
FIG. 11 is a SEM micrograph of a Ti surface modified with a TCP coating layers using LENS™ at 400W laser power, 15 mm/sec. scan speed and 13 g/min. powder feed rate, and after polishing and etching in accordance with an embodiment of the disclosure.

FIG. 11 is a SEM micrograph of a Ti surface modified with a TCP coating layer using LENS™ at 400 W laser power, 15 mm/sec. scan speed and 13 g/min. powder feed rate, and after polishing and etching in accordance with an embodiment of the disclosure. As shown in FIG. 11, the composite coating surface is crack-free and contains uniformly distributed TCP particles. Moreover, the coating surface has a rough appearance, which in some embodiments, can be advantageous to bone tissue bonding in vivo. In this example, polishing and etching reveals the distribution of TCP in the coating layer. It can be seen from FIG. 11 that TCP is evenly distributed in the coating with sizes ranging from 8-12 μm. Using contrast imaging software (not shown), it was found that almost 65-70% of the surface consists of TCP. Therefore, a gradient in TCP volume fraction from 0% to at least 65% by volume was achieved within 250 μm coat thickness. Additionally, this example illustrates that TCP can extend across the surface of the composite coating layer and can have a continuous structure.

Substrate evolution from a liquid metal to a microstructural composite layer is governed by the ratio of a temperature gradient (G) to a solidification rate (R), i.e.; (G/R) [2]. The growth rate of a microstructure in a composite layer can be determined by the amount of undercooling below the melting point of the specific metal (e.g., a metal casting phenomenon). Due to rapid heat transfer at the interface of molten Ti and unmelted Ti, the rate of nucleation of the metal predominates over the rate of growth of the microstructure. This effect can result in a thin region of fine Ti grains located at the metal-coating layer interface. As the effect of undercooling diminishes as the distance away from the unmelted Ti interface increases, the rate of nucleation of the molten metal decreases. For example, as the latent heat of fusion is being released, the more exterior positioned liquid Ti can remain in a molten state. Moreover, TCP particle buoyancy can further reduce the TCP load near the interface as well as further promote microstructure growth at increasing distances away from the interface. This microstructure growth is controlled by the rate of heat transfer from the interface. Because the above-described phenomenon establishes a temperature gradient towards the interface, the microstructure growth occurs in a direction opposite to the heat flow. The effect is the formation of columnar grains at the interface [4]. These columnar grains advance towards the surface of the coating. However, near the surface of the composite coating layer, heterogeneous nucleation is a predominating factor due to the presence of a high volume fraction of TCP. As a result, the exterior upper region of the composite coating layer consists of mostly fine equiaxed grain structures.

As mentioned, the density difference between TCP and Ti can play a role in the distribution of TCP. Because the density of TCP (3.07 g/cc) is lower than the density of Ti (4.5 g/cc), the TCP particles may exhibit buoyancy behavior in the molten Ti metal pool. The movement of the solid-liquid interface during the solidification process, which is governed by the cooling rate, can determine the entrapment of TCP in the various sub-layers of the composite coating [5, 6]. At the lower regions of the composite coating layer (e.g., near or at the coating-substrate interface), where the solidification rate is high, the fast advancement of the solid-liquid interface can push the TCP particles upward leading to a lower volume fraction of TCP near the metal substrate (e.g., at or near the coating-substrate interface. While ascending through the molten metal pool, the solidification rate and the movement of the solid-liquid interfaces decreases. The slower movement of this interface can entrap a greater amount of TCP near and at the upper, exterior regions of the composite coating.

Hardness of the Coating Layers

EXAMPLE 14

Figure 12:
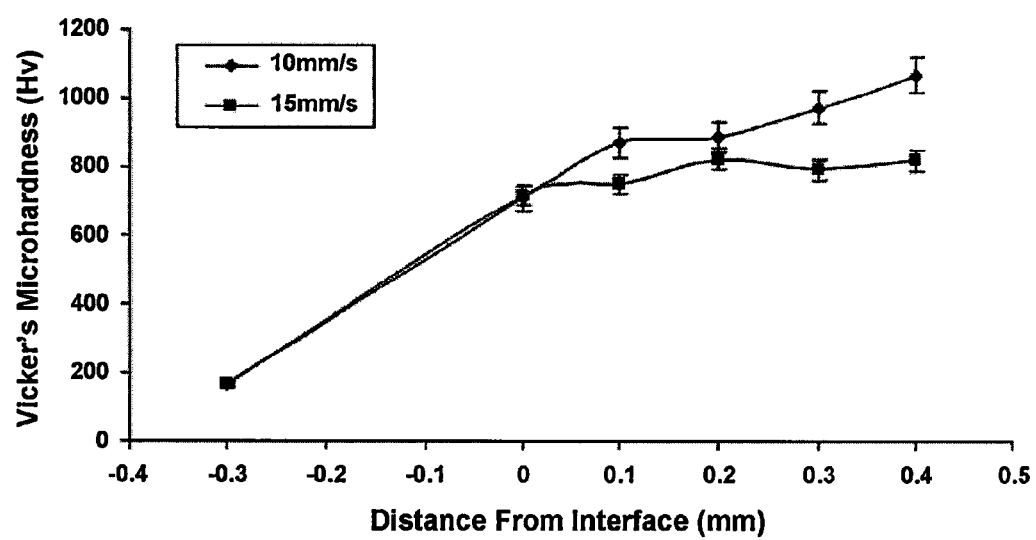
FIG. 12 is a graphical representation of hardness profiles of TCP coating layers formed using LENS™ at 500W laser power and a powder feed rate of 13 g/min. in accordance with an embodiment of the disclosure.

FIG. 12 is a graphical representation of hardness profiles of TCP coating layers formed using LENS™ at 500 W laser power and a powder feed rate of 13 g/min. in accordance with an embodiment of the disclosure. As shown, the microhardness of the TCP coatings increase from 200±18 Hv at the coating-metal substrate interface to an average value of 902±200 Hv in the upper, exterior regions of the composite coating. In this example, the gradual increase in hardness from the coating-metal substrate interface to the upper, exterior regions of the coating layer can be a result of microstructural variation across the coating thickness.

The combined effect of fine equiaxed grains and a high volume fraction of TCP at the exterior regions of coating layer can result in significantly greater hardness values. Hardness of the coating layer in the intermediate regions may be attributed to the formation of a particulate composite of TCP and Ti. According to the microstructural analysis described above with respect to Examples 11-13, the decrease in hardness at or near the coating-metal substrate interface can be attributed to elongated, columnar Ti grains and a low volume fraction of TCP.

The physical properties (e.g., thickness, volume fraction of TCP) and microhardness data for the TCP coatings, prepared with different laser parameters, are summarized in Table 4.

TABLE 4

Compilation of coating layer properties as a function of LENS ™ parameters

| LENS ™ Parameters | | | | | |
|---|---|---|---|---|---|
| Laser Power (W) | Laser Scan Speed (mm/sec.) | Powder Feed Rate (g/min.) | Thickness (μm) | TCP Volume Fraction | Ave. Coating Hardness (Hv) |
| 400 | 15 | 13 | 250 | Low | 706 ± 25 |
| 500 | 15 | 13 | 400 | High | 781 ± 70 |

TABLE 4-continued

Compilation of coating layer properties as a function of LENS™ parameters

| LENS™ Parameters | | | | | |
|---|---|---|---|---|---|
| Laser Power (W) | Laser Scan Speed (mm/sec.) | Powder Feed Rate (g/min.) | Thickness (μm) | TCP Volume Fraction | Ave. Coating Hardness (Hv) |
| 500 | 10 | 13 | 375 | High | 902 ± 180 |
| 500 | 10 | 9 | 220 | Low | 648 ± 118 |

Composition and Phase Analysis

In one embodiment, the presence of interconnected pores within the TCP powder provides high powder surface area. For example, the TCP powder having a particle size ranging from 45 to 150 μm, showed a BET surface area of 58.2±4.6 m²/g.

EXAMPLE 15

Figure 13:
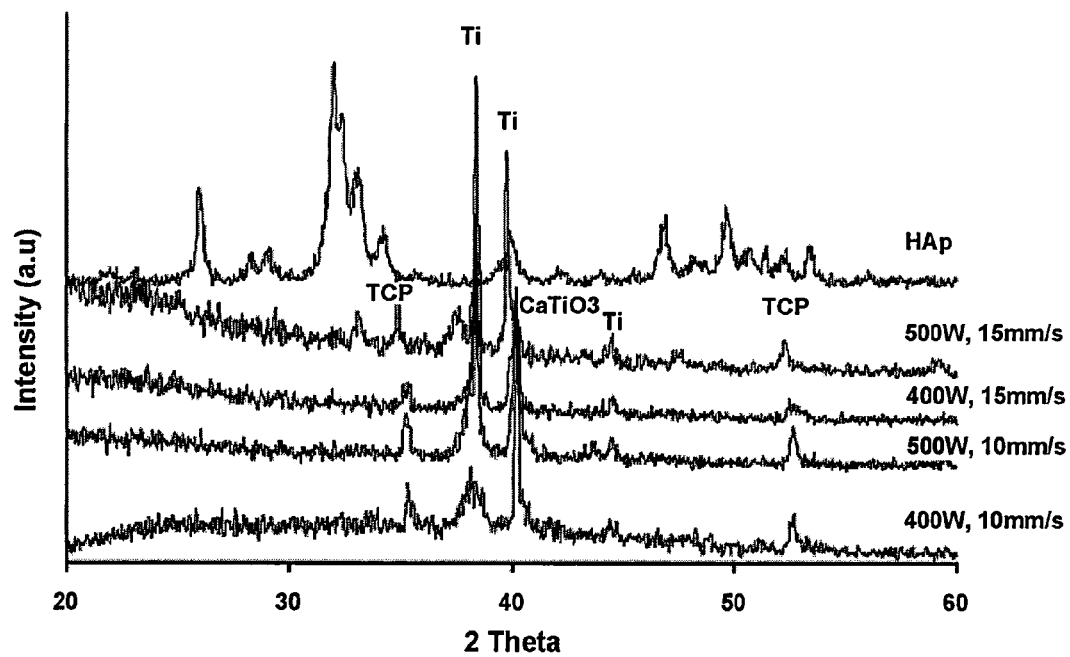
FIG. 13 is a graphical representation of X-ray diffraction spectra of TCP coating layers using LENS™ and with a powder feed rate of 13 g/min. in accordance with an embodiment of the disclosure.

FIG. 13 is a graphical representation of X-ray diffraction spectra of TCP coating layers using LENS™ and with a powder feed rate of 13 g/min. in accordance with an embodiment of the disclosure. As shown in FIG. 13, the dominant characteristic peaks were identified as Ti and TCP. During laser interaction, TCP is generated by the high temperature processing of precursor calcium phosphate as hydroxyapatite primary phase. A small peak corresponding to calcium titanate ($CaTiO_3$) was also observed in the coating. It was found that the formation of this calcium titanate phase was independent of laser parameters. The sharp peaks in the XRD patterns indicate that the TCP in the coatings are mostly crystalline in nature. Additionally, the presence of TCP particles on the surface was confirmed by EDS analysis (not shown).

Dissolution kinetics of a material is governed by its crystallinity with other solution parameters like temperature, pH, etc. Calcium phosphate-based ceramic shows higher dissolution tendency with a decrease in crystallinity. It is desirable to have a highly crystalline TCP phase in the coating because the crystalline structure can provide the coating with more stability. In contrast to Ti, TCP is a non-laser absorbing material and does not melt during laser processing using LENS™. The LENS™ process is very different from traditional reaction heating methods due to its unique characteristics such as a ultrahigh heating rate and a rapid solidification rate. Due to these characteristics, TCP retains its crystallinity in the coating, which is a property difficult to achieve in commercial coating processes like plasma spray.

As previously explained, during the LENS™ process, the laser beam is focused onto the surface of the Ti substrate. The high energy of the laser beam locally melts the Ti surface and creates a molten pool which is maintained during the laser irradiation. Simultaneously, the added powder material injected into the molten pool partially melts by interaction with the laser and also the hot molten metal. Due to the high temperature processing, HAp phase in the added powders reacts to form TCP. The high temperature process also induces interactions between HAp and $TiO_2$ leading to formation of various compounds. High temperature phases that can form between CaO and $TiO_2$ are $Ca_3Ti_2O_7$, $CaTiO_3$, $Ca_4Ti_3O_{10}$ and $Ca_5Ti_4O_3$ [2, 3]. For example, possible reactions between HAp and Ti are as follows:

$HAp + TiO_2 \rightarrow CaTiO_3 + TCP + H_2O$

$TCP + TiO_2 \rightarrow CaTiO_3 + \alpha\text{-}Ca_2P_2O_7$

$\alpha\text{-}Ca_2P_2O_7 + Ti \rightarrow CaTiO_3 + CaO + P_2O_3(g)\uparrow$

The presence of $CaTiO_3$ was detected in the XRD pattern (shown in FIG. 13). However, the amount of this phase formation can be governed by the interaction time between Ti and TCP. Since LENS™ is characterized by rapid heating and cooling rates, the interaction time is relatively short. Therefore, by optimally choosing appropriate LENS™ parameters, these coatings can be made with a highly crystalline TCP phase along with a small amount of other phases.

Morphology of OPC1 Cells on TCP Coating

In one embodiment, evaluation of the biological activity of TCP coatings can be performed using TCP-coated Ti substrate samples seeded with human osteoblast cells (HOCs).

EXAMPLE 16

In this example, the Ti samples were sterilized by autoclaving at 121° C. for 20 minutes. The cells used in this example were derived from an immortalized, osteoblastic precursor cell line (OPC1) established from human fetal bone tissue. For routine maintenance, cells were plated at a density of $10^5/cm^2$ in 100 mm tissue culture plates (Cellstar, Greiner Bio-one, Germany) and cultured in McCoy's 5A Medium (enriched with 5% fetal bovine serum, 5% bovine calf serum and supplemented with 4 μg/ml of fungizone). The cells were seeded onto coated Ti samples and uncoated Ti control samples placed in 6 well plates and maintained at 37° C. under an atmosphere of 5% $CO_2$ and 95% air. The culture medium in the plates was changed every 2 days. In this example, all OPC1 cells originated from the same cell line passage and all plates were kept in identical conditions.

The coated and uncoated Ti samples were removed from culture after either 5 or 11 days of cell-sample co-incubation. Morphology of the OPC1 cells were subsequently assessed by SEM. Samples were rinsed with 0.1 M phosphate-buffered saline (PBS) and subsequently fixed with 2% paraformaldehyde/2% glutaraldehyde in 0.1 M cacodylate buffer overnight at 4° C. Following a rinse in 0.1 M cacodylate buffer, each sample was postfixed in 2% 6 osmium tetroxide ($OsO_4$) for 2 hours at room temperature. Fixed samples were then dehydrated in an ethanol series (e.g., 30%, 50%, 70%, 95% and 100%) three times, followed by a hexamethyl-disililane (HMDS) drying procedure. Dried samples were gold coated (Technics Hummer, San Jose, Calif.), and observed using a Hitachi s-570 SEM.

Figure 14A:
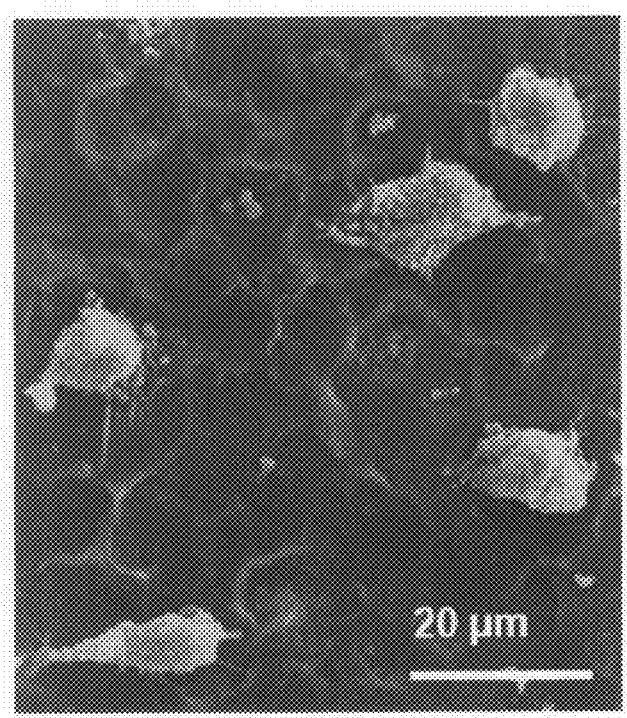
FIGS. 14A-D are SEM micrographs illustrating OPC1 morphology and cell adhesion on Ti substrates after 5 days incubation in cell culture with (A) uncoated Ti, and (B) TCP coated Ti; and after 11 days incubation in cell culture with (C) uncoated Ti, and (D) TCP coated Ti in accordance with an embodiment of the disclosure.
Figure 14B:
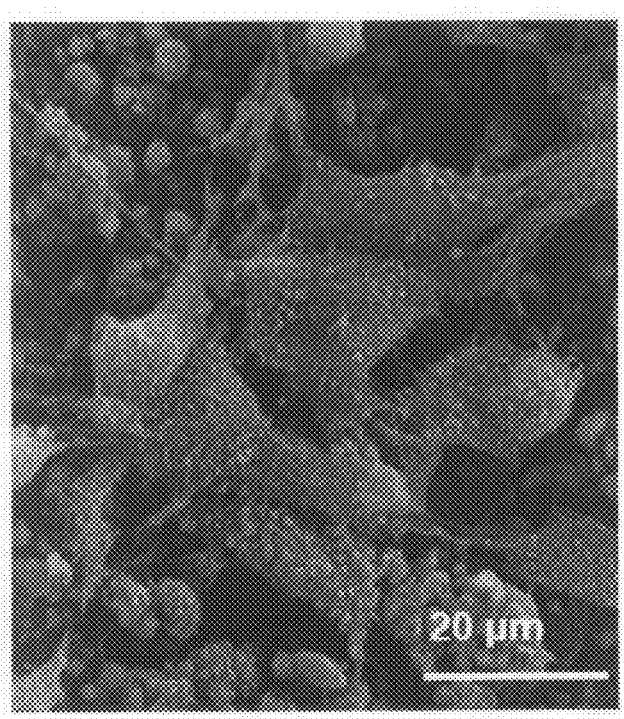
Figure 14C:
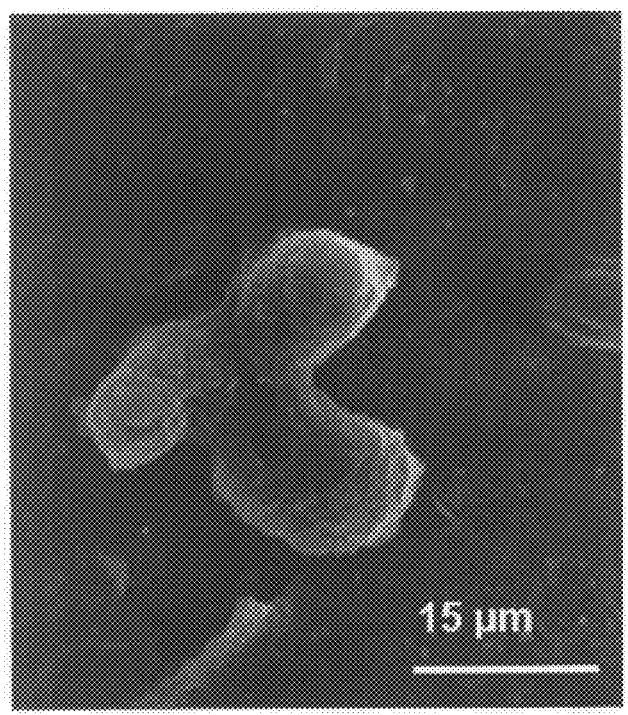
Figure 14D:
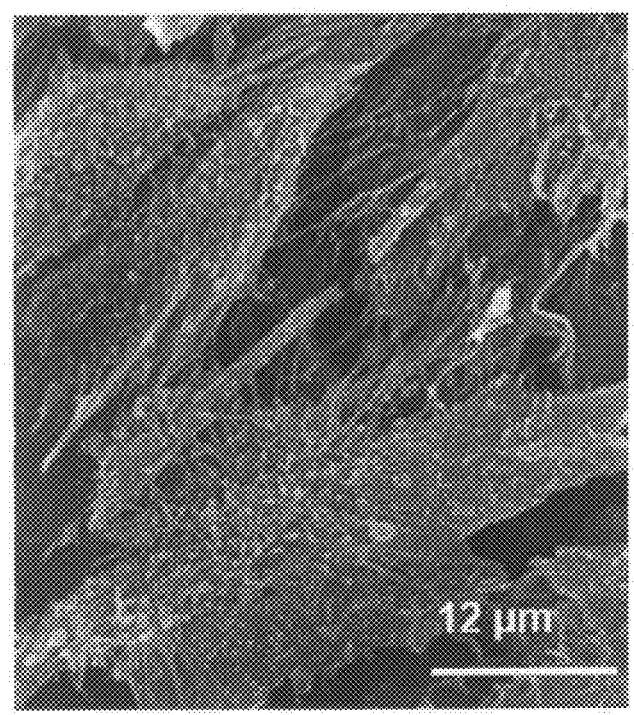

FIGS. 14A-D are SEM micrographs illustrating OPC1 morphology and cell adhesion on Ti substrates after 5 days incubation in cell culture with (A) uncoated Ti, and (B) TCP coated Ti; and after 11 days incubation in cell culture with (C) uncoated Ti, and (D) TCP coated Ti in accordance with an embodiment of the disclosure. When comparing OPC1 morphology and cell adhesion following 5 days of incubation, there are more OPC1 cells attached to the surface of the TCP coated substrates than the uncoated substrates. For example, cells attached to the TCP coating, as shown in FIG. 14B, have cell edges with a diffuse, spread-like morphology with several lamellipodia and filopodia extensions, while FIG. 14A shows that the uncoated Ti surface has very little cell spreading. This cell attachment trend continues with additional incubation time. For example, cell layers were formed on TCP coatings after 11 days of culture, as shown in FIG. 14D. Additionally, extracellular matrix (ECM) (seen as spherical granules on the surface of the cells, which is an indication of mineralization) was formed by the cells attached to the TCP-coated Ti substrates, but not by the cells attached to the uncoated Ti samples.

Cell Survival and Proliferation

Cell survival and proliferation can also be considered in a determination of metal implant material in vitro biocompatibility.

EXAMPLE 17

In this example, cell proliferation of OPC1 cells on coated and uncoated Ti samples were assessed by MTT assay (Sigma, St. Louis, Mo.). Similarly to the MTT assay described above with respect to Example 4, an MTT solution of 5 mg/ml was prepared by dissolving MTT in PBS followed by filter sterilization. The MTT solution was diluted (50 µl into 450 µl) in serum free, phenol red free Dulbeco's Minimum Essential medium (DME). Diluted MTT solution was then added to each sample. Following 2 hours of sample incubation with OPC1 cells in the MTT solution, a solvent solution made up of 10% Triton X-100, 0.1 N HCl and isopropanol was added to dissolve the resultant formazan crystals. In this example, 100 µl of the resulting supernatant was transferred into a 96-well plate and read by a plate reader at 570 nm. Data are presented as mean i standard deviation.

Figure 15:
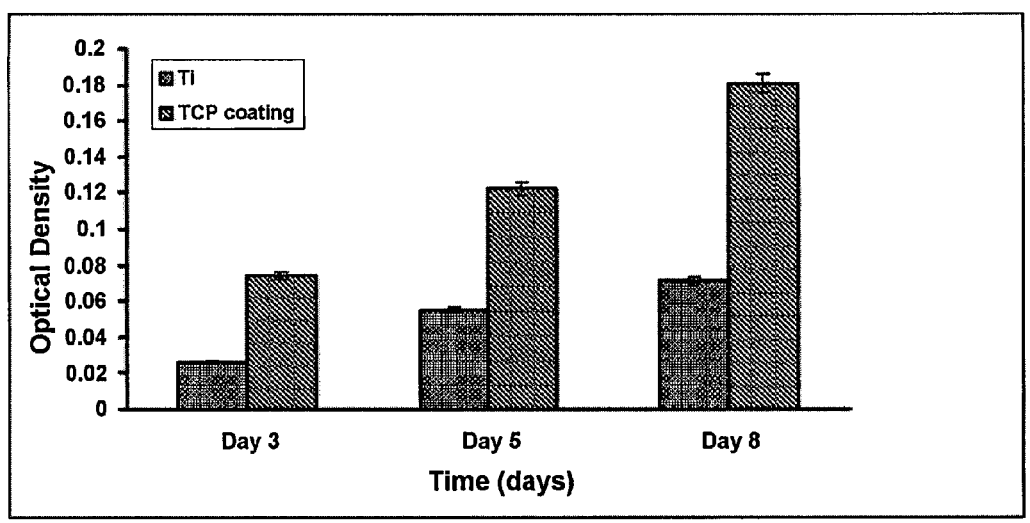
FIG. 15 is a graphical representation of OPC1 cell proliferation on TCP-coated Ti substrates and uncoated Ti substrates in accordance with an embodiment of the disclosure.

FIG. 15 is a graphical representation of OPC1 cell proliferation on TCP coated Ti substrates and uncoated Ti substrates in accordance with the above-described MTT assay. As shown in FIG. 15, cell proliferation was evident over the duration of the experiment (e.g., over 3, 5 and 8 days of cell incubation). In the present example, data from the MTT assay showed that the number of cells on TCP-coated Ti substrates is consistently greater than the number of cells on uncoated Ti substrates. Statistical analysis was performed using Student's t test, and p <0.05 was considered statistically significant for this example. The statistical analysis showed significant differences in cell proliferation on the TCP-coated samples after 3, 5 and 8 days in cell culture The results also demonstrated significant differences in cell proliferation on TCP-coated Ti samples when compared to uncoated Ti control samples for all time periods tested.

The physical and biological properties of bioceramic-coated metal substrates examined in Examples 6-17 indicate that different coating properties can be achieved by suitably selecting the process parameters. For example, a bioceramic composite coating prepared using a high laser power, high powder feed rate and low scan speed can yield a high volume fraction of coating material having a high level of microhardness and good bone cell-materials interactions.

Preparation of Calcium Phosphate Coating with Deposited Ag

EXAMPLE 18

In this example, commercial grade calcium phosphate powder, mainly HAp as primary phase, having particle size ranging from 45 to 150 µm was used to coat 0.89 mm thick Ti substrate (Alfa Asear) of 99.7% purity. Ti substrate was first cleaned with acetone to remove organic materials from the surface prior to coating. LENS™ 750 (Optomec, Albuquerque, N. Mex., USA) unit with 0.5 kW continuous wave Nd:YAG laser was used to process TCP coatings on Ti substrate. Detailed discussion of TCP coating on Ti using LENS™ has been discussed earlier [15]. TCP coated samples were cleaned with acetone and distilled water prior to Ag electrodeposition. The electrodeposition was performed from an aqueous solution of $AgNO_3$ at 5 V for 2 min. using platinum as anode. Different concentrations of silver nitrate solution were used as electrolyte for the Ag-electrodeposition and are summarized in Table 5.

TABLE 5

| Deposition conditions of Ag deposited samples | |
|---|---|
| Serial number | Deposition condition |
| S1 | 0.001 M $AgNO_3$ solution |
| S2 | 0.1 M $AgNO_3$ solution |
| S3 | 0.5 M $AgNO_3$ solution |
| S4 | No Ag coating |

As the deposition voltage and time remains constant, different concentrations of $AgNO_3$ solution will deposit a varying amount of Ag on the TCP coated surfaces. Surface and cross-sectional morphology of the coating was studied using scanning electron microscope (SEM) fitted with an energy dispersive spectroscopy (EDS) detector (not shown).

Antimicrobial Tests

EXAMPLE 19

To determine antimicrobial activity, TCP coated samples, with and without deposited silver, from Example 18 were challenged individually with *Pseudomonas aeruginosa* and *Staphylococcus aureus*. Samples were placed in a multi-well plate (FALCON brand), with one sample per well and appropriately labeled. Trypticase soy agar (TSA) culture medium was used to prepare TSA plates for growing surviving bacterial colonies. For bacterial dilutions, sterile saline (0.85% sodium chloride in water) was used. The media M101, consisting of M110 plus 0.1% yeast extract, 10% glucose, 0.1% neopeptone, 25% M101 and 1.0% Bovine serum in water was used as challenge media.

To each well 4 ml of inoculum prepared in M101 or M110 medium (for *P. Aeruginosa* and *S. aureus*, respectively) was added. The inoculum was prepared by adding overnight culture of bacteria to M101 or M110 medium in proper dilution that would yield an initial inoculum of $\sim 1\times 10^5$ cfu/ml. The multi-well plate was then incubated at 37° C. for 24 h. The fluid from each well was appropriately diluted and plated on TSA plates. Coated samples were plated at $10^{-1}$, $10^{-2}$ and $10^{-3}$ dilutions. The zero time point samples and control samples (e.g., S4 samples from Table 5) were plated at $10^{-3}$, $10^{-5}$ and $10^{-7}$ dilutions. The samples were incubated at 37° C. for 48h and surviving colonies counted. From the initial inoculum dose obtained from zero time plate count and surviving bacteria count, log reduction values were calculated.

Table 6 shows the antimicrobial efficacy of the TCP and Ag-TCP coatings following a 24 hour *Pseudomonas aeruginosa* and *Staphylococcus aureus* challenge assays. The TCP coatings having no Ag deposition (S4), show no antimicrobial activity against *P. aeruginosa* or *S. aureus*. However, the Ag-TCP coatings S2-S3 show strong antimicrobial activity against both bacterial strains, and sample S1 shows strong antimicrobial activity against *P. aeruginosa*. Log reduction in bacteria due to Ag coating is estimated as logarithm of ratio of initial bacterial colonies to average final surviving colonies. Log reductions >4, equates to a >99.99% reduction in bacteria, is counted as strong antimicrobial activity. Therefore, all of the Ag-TCP coatings show very strong antimicrobial activity towards *Pseudomonas aeruginosa*, whereas TCP coatings without Ag show an increase in bacterial colonies. A reduction in antimicrobial activity can be noticed for samples S1 with low Ag content when compared to samples (S2, S3) with greater Ag content. However, as shown in Table 6, the antimicrobial activity does not improve with Ag deposition solutions having greater than 0.1 M AgNO₃ solution, as evidenced by the similarity in results between S2 and S3 samples.

tions demonstrated that the TCP coating is non-toxic, and thus, does not inhibit cell proliferation.

D. References

The following references are herein incorporated by reference.

TABLE 6

Antimicrobial efficacy of the silver treated titanium discs. A 24 h *Pseudomonas aeruginosa* ATCC 9027 and *Staphylococcus aureus* ATCC 33591 challenge assay. Values are the log reduction obtained as an average of a triplicate assay.

| Sample | Log of zero time inocula | | Log survivors (triplicate) | | Log reduction | |
|---|---|---|---|---|---|---|
| | *P. aeruginosa* ATCC 9027 | *S. aureus* ATCC 33591 | *P. aeruginosa* ATCC 9027 | *S. aureus* ATCC 33591 | *P. aeruginosa* ATCC 9027 | *S. aureus* ATCC 33591 |
| S1 | 5.5 | 5.8 | 1.78 | 5.3 | 5.41 | 2.48 |
| S2 | 5.5 | 5.8 | 1.48 | 2.66 | 5.71 | 5.12 |
| S3 | 5.5 | 5.8 | 1.48 | 2.78 | 5.71 | 5.00 |
| S4 | 5.5 | 5.8 | 7.18 | 7.78 | N/A | N/A |

Although Ag is well known as a strong antimicrobial agent, high concentrations of Ag have been reported to be cytotoxic. It is reported that the toxicity of Ag ions affect the basic metabolic cellular functions of all specialized mammalian cells. Therefore, it is useful to incorporate a minimum amount of Ag on medical implant surfaces to minimize this tissue cytotoxicity effect, while maintaining a high level of antimicrobial activity. In accordance with an embodiment of the disclosure, the Ag-TCP coating prepared from 0.1 M AgNO₃ solution has an enhanced antimicrobial property combined with good natural bone cell proliferation.

Discussion of LENS™ Processing

Conventional plasma spray processes produce a coating of 150-200 μm thick. In contrast, TCP coatings resulting from LENS™ processing can have thickness varying from approximately 200-700 μm, or in another embodiment, from approximately 100-900 μm. Moreover, the volume fraction of TCP in the coating can be tailored by suitably selecting the processing parameters like laser power, laser scan speed and powder feed rate (see Tables 3 and 4). While plasma spray processes can only produce a thick TCP layer on top of the metal substrate, LENS™ processing can produce a compositional gradient coating. By using a LENS™ coating process, deposition of successive layers (e.g., creating a multilayer coating) can be used to develop a compositional gradient coating starting from pure Ti at the core to pure TCP on the surface with a Ti-TCP intermixed region in between.

As described above, human osteoblast cell behavior on the TCP coating was characterized by an OPC1 cell morphology study using SEM. Cell attachment is one stage of bone cell-materials interaction. Cells attach to and migrate across the material surfaces by a variety of cellular mechanisms such as extension of filopodia and lamellipodia. In one example, cell morphology, as examined by SEM, showed that filopodia extensions from the cells to the substrate are more pronounced for TCP coated surfaces. This result demonstrates that TCP coating promotes better cell attachment and spreading behavior compared to uncoated Ti. SEM observation also revealed the presence of extracellular matrix (ECM) on the TCP coatings, which can be an indication of cell differentiation. For example, the formation of ECM indicates that OPC1 cells on TCP coatings are capable of producing a matrix suitable for mineralization and can suggest the initiation of an intracellular biomineralization pathway. Another determining factor of successful bone cell-materials interactions can be cell proliferation, which is also an indication of cell survival. As described above, the MTT assay and SEM observa-

[1] Gefen, A., Med. Biol. Eng. Comput., 2002; 40:311-322.
[2] Wang Y C, Li Y M, Yu H L, Ding J, Tang X H, Li J G, Zhou Y H. Surf & Coat Tech., 2005; 200:2080-2084.
[3] Lusquiños F, Pou J, Arias J L, Boutinguiza M, León B, Pérez-Amor M, Driessens F C M, Merry J C, Gibson I, Best S, Bonfield W. J Appl Phys., 2001; 90 (8):4231-4236.
[4] Heine R W, Loper C R, Rosenthal P C. McGraw-Hill Book Company 1967.
[5] Chao M J, Niu X, Yuan B, Liang E J, Wang D S. Surf & Coat Tech., 2006; 201:1102-1108.
[6] Yang S, Chen N, Liu W, Zhong M, Wang Z, Kokawa H. Surf & Coat Tech., 2004; 183:254-260.
[7] Gong D, Grimes C A, Varghese O K, Chen Z, Hu W, Dickey E C, J. Mater. Res., 2001; 16:3331-3334.
[8] V. Parkhutik P, Shershulsky V I, J. Phys. D: Appl. Phys., 1992; 25:1258-1263.
[9] Das K, Ph.D Thesis, Washington State University, May 2007.
[10] Zhang Z W, Rare Metal Mater. Eng. 1 1996; 1:49.
[11] Peterwig H G, Pharmacol. Ther., 1996; 69:127.
[12] Rahn R O, Landry L C, Photochem. Photobiol., 1973; 8:29.
[13] Valle B O, Ulmer D D, Annu. Rev. Biochem., 1972; 41:91-128.
[14] Ritchie J A, Jones C L, Lett. Appl. Microbiol., 1990; 11:152.
[15] Roy M, Krishna B V, Bandyopadhyay A, Bose S, Acta Biomaterialia, 2008; 4 (2): 324-333.
[16] Das K, Bose S, Bandyopadhyay A, Acta Biomaterialia, 2007; 3 (4): 573-585.

E. Conclusion

The present disclosure describes methods for modifying the surfaces of metal implantable materials, such as titanium (Ti) substrate surfaces, and the modified metal materials formed therefrom. Some of the embodiments of modified metal implantable materials were evaluated for their respective physical and biological properties, including those properties useful for surgical implants. In one embodiment, metal implantable materials (e.g., Ti metal materials) can be oxidized (e.g., thermally oxidized, electrochemically oxidized) to form a titanium oxide layer on the material surface. For example, the metal implantable material can be anodized in an electrolytic solution containing sodium fluoride and sulfuric acid, to form a titania nanotube morphology on the substrate surfaces. The oxidized surface, with or without silver deposition, can provide an improved surface for cellular attachment, supported high cellular proliferation rates and enhanced bone cell-materials interactions in comparison to the cellular behavior associated with non-modified Ti-control surfaces. Furthermore, silver (Ag) coated surfaces demonstrate antimicrobial properties as evidenced by their ability to effectively inhibit greater than 99% of *Pseudomonas aeruginosa* colony growth. In contrast, Ti substrate surfaces, with or without $TiO_2$ nanotube microstructures or films, demonstrated no inhibitory properties against colony formation and growth of *P. aeruginosa*.

In other embodiments, methods disclosed herein can be used for forming calcium phosphate-based bioceramic coatings on metallic implants. In one embodiment, a LENS™ process can be used to apply a calcium-based bioceramic composite coating layer to metal surfaces. In some embodiments, a coating thickness of approximately 50 µm to 900 µm having a desirable and/or selectable amount of calcium-based bioceramic material distributed within the coating can be achieved. Additionally, the LENS™ process can be used to create coatings having a composition gradient across the coating thickness. Such composition gradients can significantly reduce the interfacial problems associated with a sharp interface, such as those present when using conventional coating processes (e.g., plasma spray). Microstructure formation varies within the composite coating layer created using the LENS™ process (e.g., columnar Ti grain structures can be more prevalent in regions closer to the composite coating-metal interface and equiaxed Ti grain structures can be more prevalent in regions closer to the exterior of the coating layer).

Microstructure variance along a coating layer thickness can be, at least in part, due to the ratio of temperature gradient to solidification rate (G/R) generated during the LENS™ process. In some embodiments, the microstructure variance and bioceramic loading can increase a coating layer hardness value. In one specific example, formation of fine Ti grain structures, along with TCP presence at the grain boundaries, increased the coating hardness to approximately 1049±112 Hv compared to an unmodified substrate hardness of 200±15 Hv. In vitro studies indicate that calcium-based bioceramic composite coatings, such as TCP coatings, have good biocompatibility with OPC1 cells. For example, the coating surface promotes OPC1 cell attachment and proliferation. In some arrangements, the coating can also promote biomineralization.

In accordance with some arrangements, a metal implant and/or metal substrate can include a calcium-based bioceramic coating with varying thickness. For example, the coating may have a first thickness at a first surface region of the metal substrate and a second thickness at a second region of the metal substrate. Moreover, the coating characteristics, other than thickness, at a first region of the metal substrate (e.g., microhardness, microstructure, volume fraction of bioceramic particles, and other biophysical and biochemical properties) can be the same or different from other regions of the metal substrate.

Furthermore, a bioceramic coating on the surface of a metal implant can have a complex pattern of modified regions and unmodified regions as well as have differences in the resulting modifications between the regions. In one embodiment, one or more regions of a metal implant may be modified with a titania nanotube microstructure with a silver coating, and in another region of the metal implant, a bioceramic coating can be formed. In other embodiments, regions modified with a titania nanotube microstructure with a silver coating can be partially or completely overlapping with regions having a bioceramic coating.

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or methods described herein. While some processes are described in a given order, alternative embodiments may perform methods having steps in a different order, and some processes may be deleted, moved, added, subdivided, combined, and/or modified. Accordingly, each of these methods may be implemented in a variety of different ways. Also, while some methods (e.g., surface modification methods) are at times shown as being performed in series, these methods may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

We claim:

1. A metal device for attaching to bone, the device comprising:
a composite metal implant configured to be implanted in the body;
a first surface region in continuous contact with the composite metal implant, wherein the first surface region comprises titania nanotube microstructures with an inner diameter greater than 100 nm; and
an antimicrobial agent on the first surface region.

2. The device of claim 1, wherein the antimicrobial agent is particles of elemental silver, and wherein the particles have a particle size of approximately 1 nm to approximately 100 microns.

3. The device of claim 2 wherein the titania nanotubes are formed by an anodization process and the silver is electrodeposited on the nanotubes.

4. The device of claim 1 wherein the device inhibits bacterial growth.

5. The device of claim 1, further comprising a calcium phosphate-based bioceramic surface coating on a second surface region of the composite metal structure.

6. The device of claim 5 wherein the surface coating has a coating thickness of approximately 50 nm to approximately 900 μm.

7. The device of claim 5 wherein the first surface region is adjacent to the second surface region.

8. The device of claim 5 wherein the first surface region and the second surface region are at least partially overlapping.

9. An implantable medical apparatus, comprising:
a metal implant configured to be attached to bone;
a first surface region in continuous contact with the metal implant, wherein the first surface region comprises titania nanotube microstructures with an inner diameter greater than 100 nm;
a calcium phosphate-based bioceramic surface coating layer on the first surface region, wherein the surface coating layer includes a metal-calcium phosphate composite having a plurality of microstructures formed in the surface coating layer; and
an antimicrobial agent on the first surface region.

10. The apparatus of claim 9 wherein the surface coating has first and second portions, and wherein the first portion has a first coating thickness and the second portion has a second coating thickness.

11. The apparatus of claim 9 wherein at least 60% of the calcium phosphate-based bioceramic surface coating layer includes one or more of tricalcium phosphate, tetra-calcium phosphate and hydroxyapatite.

12. The apparatus of claim 11 wherein the calcium phosphate-based bioceramic surface coating layer includes at least tricalcium phosphate, and wherein the tricalcium phosphate includes a crystalline form of tricalcium phosphate to increase a surface coating layer stability.

13. The device of claim 9 wherein the composite metal structure includes titanium metal, and wherein the calcium phosphate-based bioceramic surface coating includes a titanium (Ti) and calcium-phosphate (CaP) composite layer having a Ti-CaP gradient between a composite layer-Ti metal surface interface and an exterior region of the composite layer.

* * * * *